United States Patent
Larsson et al.

[11] Patent Number: 5,948,789
[45] Date of Patent: Sep. 7, 1999

[54] PROCESS FOR SYNTHESIS OF SUBSTITUTED SULPHOXIDES

[75] Inventors: Magnus Erik Larsson, Bromma; Urban Jan Stenhede, Södertälje; Henrik Sörensen, Mölnlycke; Sverker Per Oskar von Unge, Fjärås; Hanna Kristina Cotton, Årsta, all of Sweden

[73] Assignee: Astra Aktiebolag, Sodertalje, Sweden

[21] Appl. No.: 08/492,087

[22] PCT Filed: Jul. 3, 1995

[86] PCT No.: PCT/SE95/00818

§ 371 Date: Jul. 14, 1995

§ 102(e) Date: Jul. 14, 1995

[87] PCT Pub. No.: WO96/02535

PCT Pub. Date: Feb. 1, 1996

[30] Foreign Application Priority Data

Jul. 15, 1994 [SE] Sweden ................... 9402510

[51] Int. Cl.⁶ ................. A61K 31/415; A61K 31/44; C07D 401/12; C07D 235/28
[52] U.S. Cl. .............. 514/299; 514/338; 514/393; 514/395; 546/183; 546/273.1; 546/273.7; 548/303.7; 548/307.1
[58] Field of Search ............... 546/273.4, 183, 546/273.1, 273.7; 548/303.1, 307.1; 514/299, 338, 393, 395

[56] References Cited

U.S. PATENT DOCUMENTS

| | | | |
|---|---|---|---|
| 5,693,818 | 12/1997 | Unge | 546/273.7 |
| 5,714,504 | 2/1998 | Lindberg et al. | 514/338 |
| 5,776,765 | 7/1998 | Graham et al. | 435/280 |
| 5,840,552 | 11/1998 | Holt et al. | 435/118 |

FOREIGN PATENT DOCUMENTS

| | | |
|---|---|---|
| 0005129 | 4/1981 | European Pat. Off. . |
| 0247983 | 4/1987 | European Pat. Off. . |
| 4035455 | 5/1992 | Germany . |
| 9208716 | 5/1992 | WIPO . |
| 9427988 | 12/1994 | WIPO . |
| 9602535 | 7/1995 | WIPO . |

OTHER PUBLICATIONS

Yamada et al. (1994) "Syntheses and antiulcer activities . . . " Chem. Pharm. Bull. 42(3): 718–720.

Eur. J. Biochem, vol. 166, pp. 453–459 (1987) Sigrist–Nelson.

J. Am. Chem. Soc., (1994), vol. 106, pp. 8188–8193 Pitchen et al.

Tetrahedron vol. 43, No. 21, pp. 5135 to 5144 (1987) Zhao et al.

Synlett, pp. 643–650 (Nov. 1990) Kagan et al.

Tetrahedron Letters, vol. 35, No. 3, pp. 485–488 (1994) Pitchen.

*Primary Examiner*—Richard L. Raymond
*Attorney, Agent, or Firm*—White & Case L.L.P.

[57] ABSTRACT

A novel process for enantioselective synthesis of single enantiomers of omeprazole or its alkaline salts, of other optically pure substituted 2-(2-pyridinylmethyl-sulphinyl)-1H-benzimidazoles as well as of other structurally related sulphoxides or their alkaline salts. The claimed process is an asymmetric oxidation of a pro-chiral sulphide to the single enantiomers or an enantiomerically enriched form of the corresponding sulphoxide. The application also claims the enantiomeric sulphoxide products produced by the process and their use in medicine.

35 Claims, No Drawings

PROCESS FOR SYNTHESIS OF SUBSTITUTED SULPHOXIDES

This application is a 371 PCT/SE95/00818, filed Jul., 3, 1995.

TECHNICAL FIELD

The present invention relates to a process for enantioselective synthesis of the single enantiomers of substituted sulphoxides or said compounds in an enantiomerically enriched form. Such substituted sulphoxides that are suitable for being prepared by the novel process are for examples the single enantiomers of omeprazole as well as the single enantiomers of other structurally related sulphoxides. The obtained products may thereafter be converted to pharmaceutically acceptable salts thereof by conventional processes. Further, the invention also relates to some new single enantiomeric compounds which can be prepared by the novel process and their use in medicine.

BACKGROUND OF THE INVENTION AND PRIOR ART

There are a large number of patents and patent applications disclosing different substituted 2-(2-pyridinylmethylsulphinyl)-1H-benzimidazoles. This class of compounds has properties making the compounds useful as inhibitors of gastric acid secretion. For example the compound, (5-methoxy-2-[[(4-methoxy-3,5-dimethyl-2-pyridinyl)methyl]sulphinyl]-1H-benzimidazole) with the generic name omeprazole, described in i.e. EP 5129, is useful as an antiulcer agent. Other compounds of interest are for instance the compounds with the generic names lansoprazole, pantoprazole, pariprazole and leminoprazole.

These compounds as well as structurally related sulphoxides, have a stereogenic centre at the sulphur atom and thus exist as two optical isomers, i.e. enantiomers. If there is another stereogenic centre in the molecule, these compounds can exist as pairs of enantiomers. Corresponding sulphides of such compounds which already contain a stereogenic centre are not pro-chiral compounds, but chiral compounds. However, the sulphur atom in these compounds does not have asymmetry and therefore they are referred to as pro-chiral sulphides in respect of this invention.

Even though this class of chiral sulphoxides has been discussed in the scientific literature since the late seventies, there is not yet any efficient asymmetric process described for the synthesis of the single enantiomers thereof. The single enantiomers of pharmacologically active compounds have met an increased interest in the last years because of improved pharmacokinetic and biological properties. Therefore, there is a demand and need for an enantioselective process that can be used in large scale for the manufacture of the single enantiomers of pharmacologically active compounds, such as for instance optically pure, substituted 2-(2-pyridinylmethylsulphinyl)-1H-benzimidazoles.

There are processes for resolution of different substituted 2-(2-pyridinylmethylsulphinyl)-1H-benzimidazoles disclosed in the prior art. Such resolution processes are for example described in DE 4035455 and WO 94/27988. These processes involve synthetic steps wherein a diastereomeric mixture is synthesised from the racemate of the corresponding substituted 2-(2-pyridinylmethylsulphinyl)-1H-benzimidazoles. The diastereomers are then separated and finally one of the separated diastereomer is converted to the optically pure sulphoxide in a hydrolytic step.

These resolution methods involving diastereomeric intermediates, suffer from at least three fundamental disadvantages namely:

1) The substituted 2-(2-pyridinylmethylsulphinyl)-1H-benzimidazole, as a racemic intermediate, has to be further processed in a couple of reaction steps before the single enantiomers can be obtained.
2) The resolution processes described involve complicated separation steps.
3) There is a large waste of highly refined material when the unwanted stereoisomer, in the form of the opposite diastereomer, is separated and discarded.

Further, prior art describes for instance enantioselective synthesis of the single enantiomers of a sulphoxide agent Ro 18-5364, (5,7-dihydro-2-[[(4-methoxy-3-methyl-2-pyridinyl)methyl]-sulphinyl]-5,5,7,7-tetramethylindeno-[5,6-d]-imidazol-6-(1H)-one), See Euro. J. Biochem. 166 (1987) 453. The described process is based on an enantioselective oxidation of the corresponding prochiral sulphide to said sulphoxide. The experimental conditions used during the oxidation are stated to be in accordance with the asymmetric sulphide oxidation process developed by Kagan and co-workers (Pitchen, P.; Deshmukh, M.; Dunach, E.; Kagan, H. B. J. Am. Chem. Soc. 106 (1984), 8188). The authors report that the obtained crude product of the sulphoxide, showing an enantiomeric excess (e.e.) of about 30%, can be purified to an essentially optical pure sulphoxide [(e.e.) >95%] by several steps of crystallisation. However, the yields and the number of crystallisation steps are not reported.

It is of interest to note that attempts of the Applicant to repeat the experimental conditions described and reported above, in the preparation of the single enantiomers of Ro 18-5364 afforded crude sulphoxide with an enantiomeric excess of only 16%.

In order to obtain the optically pure 2-(2-pyridinylmethylsulphinyl)-1H-benzimidazoles of interest, e.g. one of the single enantiomers of omeprazole, the Applicant obtained crude sulphoxides with a typical enantiomeric excess of about 5% or even lower with the above described method; See Reference Example A, below.

In the above mentioned process for asymmetric oxidations of sulphides to sulphoxides developed by Kagan and co-workers (J. Am. Chem. Soc. (1984) cited above), the oxidation is performed by using tert.butyl hydroperoxide as oxidising agent in the presence of one equivalent of a chiral complex obtained from Ti(OiPr)$_4$/(+)-or (−)-diethyl tartrate/water in the molar ratio of 1:2:1.

Kagan and co-workers reported that sulphoxide products with the highest enantioselectivity could be obtained when sulphides bearing two substituents of very different size were subjected to an asymmetric oxidation. For instance, when aryl methyl sulphides were subjected to oxidation, it was possible to obtain the aryl methyl sulphoxides in an enantiomeric excess (e.e.) of more than 90%.

However, when the substituents attached to the sulphur atom of the pro-chiral sulphide have a more equal size, a moderate or poor enantioselectivity was obtained. For instance, when benzyl p-tolyl sulphide is subject to oxidation under the conditions proposed by Kagan and co-workers, the e.e. observed is only 7%.

There have been attempts to improve the conditions for asymmetric oxidation of sulphides. For example, Kagan and co-workers (Zhao, S.; Samuel, O.; Kagan, H. B. Tetrahedron (1987), 43, 5135) found that a higher enantioselectivity generally could be obtained if the tert-butyl hydroperoxide in the system discussed above was replaced by cumene hydroperoxide in the oxidation of the sulphide. For instance an enantiomeric excess of 96% could be obtained in the asymmetric oxidation of methyl p-tolyl sulphide.

Thus, as a proposed method for asymmetric oxidation of sulphides, Kagan used cumene hydroperoxide with the system Ti(O-iPr)$_4$/diethyl tartrate/water (1:2:1) in methylene chloride at −23° C. The authors reported a decreased enantioselectivity when the amount of titanium reagent was lower than 0.5 equivalent. (See Tetrahedron (1987) cited above.)

Using this improved asymmetric oxidation process with one equivalent titanium reagent in order to obtain the optically pure 2-(2-pyridinylmethylsulphinyl)-1H-benzimidazoles, e.g. one of the single enantiomers of omeprazole, the Applicant obtained a typical enantiomeric excess of about 10%; See Reference Example B, below.

The reaction conditions and their relevance in respect to the enantiomeric excess obtained for chiral sulphoxides in general, have also been discussed by Kagan and co-workers, See Synlett (1990), 643. For example a temperature of −20° C. was found to be required for a high enantioselectivity and in some cases as low as −40° C. was used by Kagan and co-workers to obtain the highest enantioselectivity. Further, the authors state that the enantioselectivity will be decreased when changing the organic solvent used in the oxidation from methylene chloride to for instance toluene. Methylene chloride and 1,2-dichloroethane are discussed as preferred solvents for the oxidation. It is to be noted that neither the low temperatures nor the proposed solvents are satisfactory from an industrial point of view.

Recently, a large scale asymmetric synthesis of an acyl-cholesterol acyltransferase (ACAT) inhibitor has been developed by Pitchen and co-workers (Pitchen, P; France, C. J.; McFarlane, I. M.; Newton, C. G.; Thompson, D. M. Tetrahedron Letters (1994), 35, 485). The discussed ACAT inhibitor, general named "compound RP 73163", is a chiral sulphoxide bearing one 4,5-diphenyl-2-imidazolyl group and one 5-(3,5-dimethyl-1-pyrazolyl)-1-pentyl group on the stereogenic center, i.e. the sulphur atom. However, the compound, which is not a substituted 2-(2-pyridinylmethylsulphinyl)-1H-benzimidazole type compound according to the present invention, has two large substituent groups attached to the stereogenic centre just as the compounds obtained in the present invention.

Initially, the corresponding prochiral sulphide of RP 73163, bearing these two large substituents on the sulphur atom, was oxidised using the above mentioned asymmetric oxidation method proposed by Kagan (See Tetrahedron (1987) cited above). The prepared sulphoxide is reported to be obtained in a good chemical yield but the enantiomeric excess of the sulphoxide was 0% (racemic mixture). However, these discouraging results are not surprising for a chemist since in the literature the highest enantioselectivities for the titanium tartrate mediated reactions always have been reported in the case of oxidation of rigid (e.g. cyclic) sulphides or sulphides bearing two substituents of very different size. The authors conclude that the enantioselectivity for this type of oxidations is mainly governed by steric effects.

With respect of the information disclosed in published literature and in order to have a suitable prochiral substrate for an asymmetric oxidation, Pitchen and co-workers (See Tetrahedron Letters (1994) cited above) have decided to reduce the size of one of the substituents attached on the sulphur atom in the sulphide. An intermediate of choice for such a process may be a N-protected 4,5-diphenyl-2-imidazolyl methyl sulphide which after oxidation is obtained as the corresponding sulphoxide. The enantiomeric excess of the formed sulphoxides is in the range of 98–99%. However, the synthetic route becomes more complicated using an intermediate than the originally method proposed for the asymmetric oxidition of 2-[5-(3,5-dimethylpyrazol-1-yl)pentylthio]-4,5-diphenyl imidazole. Starting from 4,5-diphenyl-2-imidazolethiol, the synthetic route has to include the following synthetic steps:

1) Methylation of the mercapto group.
2) Attaching a protective group to one of the nitrogen atoms in the imidazole moiety.
3) Asymmetric oxidation of the sulphide to a sulphoxide.
4) Reacting the obtained methyl sulphoxide derivative with a strong base, such as lithium diisopropyl amide (LDA), in order to abstract a proton from the methyl group.
5) Alkylating the lithium salt of the methyl sulphoxide derivative with 4-chloro-1-iodobutane giving a 5-chloropentyl sulphoxide derivative.
6) Attaching the pyrazolyl group to the n-pentyl chain.
7) Removing the protective group.

It is obvious that the proposed complicated approach by optimising the size of the substituents is not suitable for preparation, especially not in a large scale.

It should be noted that the process according to the present invention applied to the pro-chiral sulphide of RP 73163, surprisingly gives RP 73163 in an enantiomeric excess of >85–90%, See Reference Examples E and F, below.

The prior art literature does not disclose nor propose a suitable enantioselective process which can be used in large scale for obtaining the single enantiomers of 2-(2-pyridinylmethylsulphinyl)-1H-benzimidazoles. Therefore, there is still a long-felt demand for such an enantioselective process for the manufacture of substituted optically pure 2-(2-pyridinylmethylsulphinyl)-1H-benzimidazoles as well as other structurally related suiphoxides.

BRIEF DESCRIPTION OF THE INVENTION

The present invention provides a novel process for enantioselective synthesis of the single enantiomers of omeprazole, of other optically pure substituted 2-(2-pyridinylmethylsulphinyl)-1H-benzimidazoles as well as of other structurally related sulphoxides, in which process a surprisingly high enantioselectivity is obtained. The novel process is characterized in that a pro-chiral sulphide is oxidised asymmetrically into a single enantiomer or an enantiomerically enriched form of the corresponding sulphoxide. This novel asymmetric oxidation surprisingly makes it possible to obtain the compounds of interest with an extremely high enantiomeric excess, even if the corresponding pro-chiral sulphide has substituents on the sulphur atom of approximately the same size. The process is simple with one step of reaction making the process suitable for large scale production of enantiomeric compounds in a high yield and with a high enantiomeric excess.

The expressions "pro-chiral sulphide(s)" are used for the sulphides of the corresponding sulphoxides suitable for being prepared by the novel process according to the present invention. If the corresponding sulphide already contains a stereogenic centre in the molecule, such a sulphide is not a pro-chiral compound, but a chiral compound. Since the sulphur atom of the sulphides does not have asymmetry such a compound is referred to as a pro-chiral sulphide in the present specification and appending claims.

The present invention also provides optically pure compounds prepared in accordance with the claimed process and some novel single enantiomeric compounds.

The process of the invention is defined in claim 1 and some alternative processes are described in the independent claims 2–4. The subclaims 5–23 define some specifically preferred embodiments of the invention, and preferred products prepared by the new process are defined in claims, 31–34.

DETAILED DESCRIPTION OF THE INVENTION

The present invention provides a novel method of preparing a sulphoxide of formula I either as a single enantiomer or in an enantiomerically enriched form:

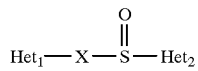

wherein
Het$_1$ is

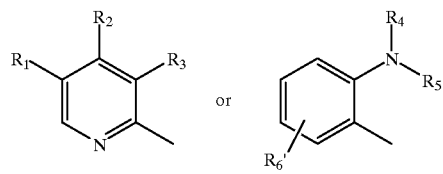

Het$_2$ is

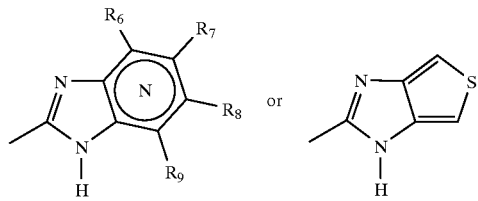

and X is

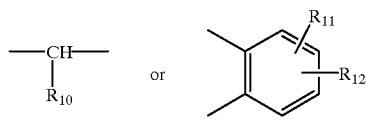

wherein
N inside the benzene ring of the benzimidazole moiety means that one of the carbon atoms substituted by R$_6$–R$_9$ optionally may be exchanged for a nitrogen atom without any substituents;

R$_2$, R$_2$ and R$_3$ are the same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

R$_4$ and R$_5$ are the same or different and selected from hydrogen, alkyl and aralkyl;

R$_6$' is hydrogen, halogen, trifluoromethyl, alkyl or alkoxy;
R$_6$–R$_9$ are the same or different and selected from hydrogen, alkyl, alkoxy, halogen, halo-alkoxy, alkylcarbonyl, alkoxycarbonyl, oxazolyl, trifluoroalkyl, or adjacent groups R$_6$–R$_9$ form ring structures which may be further substituted;

R$_{10}$ is hydrogen or forms an alkylene chain together with R$_3$ and

R$_{11}$ and R$_{12}$ are the same or different and selected from hydrogen, halogen and alkyl.

In the above definitions alkyl groups, alkoxy groups and moities thereof may be branched or straight C$_1$–C$_9$-chains or comprise cyclic alkyl groups, for example cycloalkylalkyl.

Preferably, the sulphoxides prepared by the novel method are sulphoxides of formula I' either as a single enantiomer or in an enantiomerically enriched form:

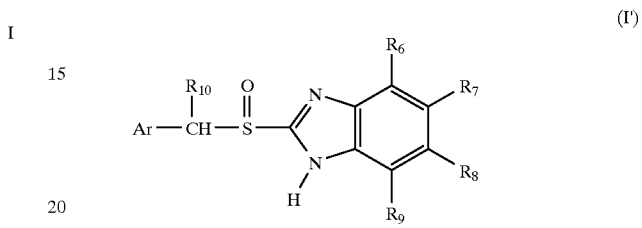

wherein

Ar is

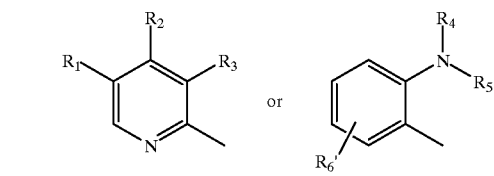

and R$_1$–R$_{10}$ are as defined above in connection with formula I.

Most preferably the sulphoxides prepared by the novel process are sulphoxides of any of the formulas Ia to Ih either as a single enantiomer or in an enantiomerically enriched form:

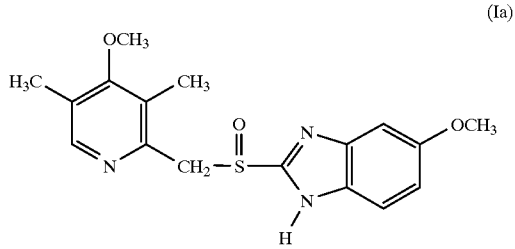

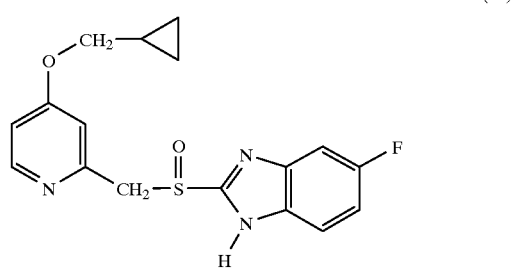

-continued

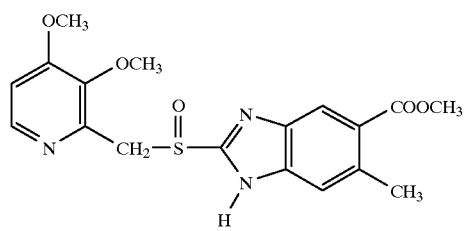
(1c)

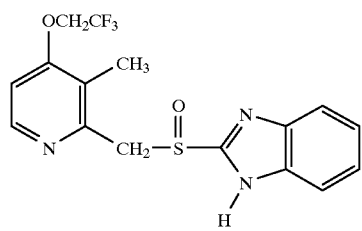
(Id)

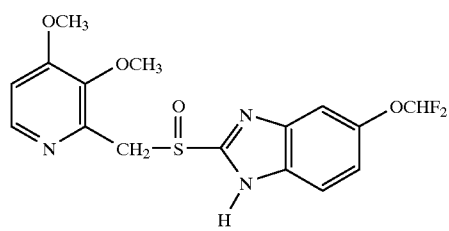
(Ie)

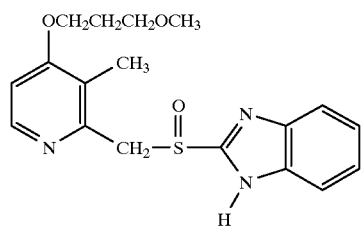
(If)

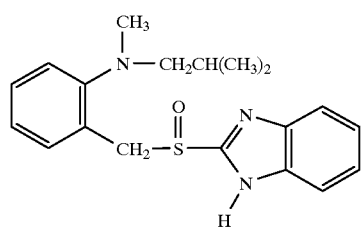
(Ig)

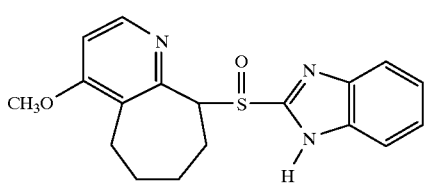
(Ih)

The compounds defined by the above formulas I, I' and Ia–Ih may be converted to pharmaceutically acceptable salts thereof by conventional methods.

The process of the present invention is characterized by an asymmetric oxidation in an organic solvent of a pro-chiral sulphide according to formula II

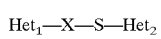   II wherein $Het_1$ and $Het_2$ are as defined above with an oxidising agent and a chiral titanium complex, optionally in the presence of a base.

According to one aspect of the invention the asymmetric oxidation is carried out in the presence of a base.

Alternatively, the oxidation can be carried out in the absence of a base if the preparation of the chiral titanium complex is performed in a specific way with respect to the order of addition, preparation temperature and/or preparation time.

Thus, according to one preferred aspect of the invention the preparation of the chiral titanium complex is performed in the presence of the pro-chiral sulphide, i e the pro-chiral sulphide is loaded into the reaction vessel before the components used for the preparation of the chiral titanium complex are loaded.

According to another preferred aspect of the invention the preparation of the chiral titanium complex is performed during an elevated temperature and/or during a prolonged preparation time.

According to still another preferred aspect of the invention the preparation of the chiral titanium complex is performed during an elevated temperature and/or during a prolonged preparation time and in the presence of the pro-chiral sulphide.

According to the most preferred aspect of the invention, the asymmetric oxidation is carried out in the presence of a base and the preparation of the chiral titanium complex is performed during an elevated temperature and/or during a prolonged preparation time and in the presence of the pro-chiral sulphide.

The oxidation is carried out in an organic solvent. Surprisingly, the solvent is not as essential for the enantioselectivity of the oxidation, as reported by Kagan and co-workers. The solvent can be chosen with respect to suitable conditions from an industrial point of view as well as environmental aspects. Suitable organic solvents are for instance toluene, ethyl acetate, methyl ethyl ketone, methyl isobutyl ketone, diethyl carbonate, tert. butyl methyl ether, tetra hydrofurane, methylene chloride and the like. From an environmental point of view non-chlorinated solvents are preferred.

The oxidation is preferably carried out in an organic solvent at room temperature or just above room temperature, e g between 20–40° C. Surprisingly, the process does not require a temperature below −20° C., as described by Kagan and co-worker as essential for good enantioselectivity. Such a low temperature results in long reaction times. However, if the reaction time is variated a reaction temperature may be chosen below as well as above the preferred temperatures 20–40° C. A suitable temperature range is limited only depending on the decomposition of the compounds, and that the reaction time is dramatically shorter at room temperature than at −20° C. since the sulphides of interest are oxidised very slowly at such a low temperature.

An oxidising agent suitable for the novel asymmetric oxidation may be a hydroperoxide, such as for example tert.butylhydroperoxide or cumene hydroperoxide, preferably the latter.

The titanium complex suitable for catalysing the process of the invention is prepared from a chiral ligand and a titanium(IV) compound such as preferably titanium(IV) alkoxide, and optionally in the presence of water. An especially preferred titanium(IV)alkoxide is titanium(IV) isopropoxide or -propoxide. The amount of the chiral titanium complex is not critical. An amount of less than approximately 0.50 equivalents is preferred and an especially preferred amount is 0.05–0.30 equivalents.

Surprisingly, even very low amounts of complex, such as for instance 0.04 equivalents may be used in the processes according to the present invention with excellent result.

The titanium complex may also be prepared by reacting titanium tetra chloride with a chiral ligand in the presence of a base.

The chiral ligand used in the preparation of the titanium complex is preferably a chiral alcohol such as a chiral diol. The diol may be a branched or unbranched alkyl diol, or an aromatic diol. Preferred chiral diols are esters or tartaric acid, especially (+)-diethyl L-tartrate or (−)-diethyl D-tartrate are preferred.

As discussed above and more in detail below, the chiral titanium complex may be prepared in the presence of the pro-chiral sulphide or before the pro-chiral sulphide is added to the reaction vessel.

As mentioned above, according to one aspect of the invention, the oxidation is carried out in the presence of a base. A surprisingly high enantioselectivity is observed when a base is present during the oxidation. This noteworthy high enantioselectivity is observed even though the substrates are pro-chiral sulphides with substituents on the sulphur atom having approximately the same size.

The base may be an inorganic or an organic base, such as for instance a hydrogen carbonate, an amide or an amine. Amine includes a guanidine or an amidine.

Organic bases are preferred and especially suitable bases are amines, preferably triethylamine or N,N-diisopropylethylamine. The amount of base added to the reaction mixture is not critical but should be adjusted with respect to the reaction mixture.

This specific feature of adding a base to the reaction mixture in order to enhance the enantioselectivity of the oxidation is exemplified by two experiments with 5-methoxy-2-[[(4-methoxy-3,5-dimethyl-2-pyridinyl)-methyl]thio]-1H-benzimidazole used as the pro-chiral sulphide for the reaction. See Reference Examples D and E. The reaction conditions are the same in both experiment, except for the addition of a base to the reaction mixture in one of the experiments. Reference Example D is performed in accordance with claim 1 of the present invention, i e the asymmetric oxidation is performed in the presence of a base. Reference Example C is performed in the absence of a base without any alteration of the process parameters. The results show that the oxidation without any addition of a base according to Reference Example C affords a sulphoxide product with an enantiomeric excess (e.e.) of 23%, while the oxidation in the presence of a base, such as diisopropylethylamine, according to Reference Example D affords a sulphoxide product with an enantiomeric excess of 78%.

Alternatively, the process of the invention can be carried out in the absence of a base. Under such conditions the processes for preparation of the chiral titanium complex are essential.

The preparation of the chiral titanium complex is preferably performed in the presence of the pro-chiral sulphide. By alter the order of addition compared to the processes disclosed in prior art the enantioselectivety of the oxidation is surprisingly enhanced.

Other essential features in the preparation of the chiral titanium complex is that the preparation of the complex is performed during an elevated temperature and/or during a prolonged time. With an elevated temperature is meant a temperature above room temperature, such as for instance 30–70° C., preferably 40–60° C. A prolonged preparation time is a period of time longer that approximately 20 minutes, preferably 1–5 hours. A suitable period of time for the preparation step depends on the preparation temperature and of the pro-chiral sulphide, optionally present during the preparation of the chiral titanium complex.

The products formed during the oxidation reaction may be extracted with an aqueous solution of ammonia or another N-containing base to avoid precipitation and/or formation of insoluble titanium salts. The aqueous phase is separated from the organic phase of the obtained mixture and the isolated aqueous phase is neutralised by the addition of a neutralising agent resulting in a protonation of the optically active sulphoxide.

Thus, another preferred feature of the process of the invention is that the titanium salts which may be formed during the process can be kept in solution by the addition of an aqueous ammonia solution. The conventional procedure described in the literature for washing out titanium salts is a treatment of the reaction mixture with water or aqueous sodium hydroxide solutions resulting in the formation of a gel which is very difficult to filter off. Another procedure for washing out the titanium salts described in the prior art, is for instance to use 1M HCl, proposed in the work by Pitchen and co-workers (Tetrahedron Letters (1994) cited above). This procedure cannot be used for products being acid labile, such as for instance 2-(2-pyridinyl-methylsulphinyl)-1 H-benzimidazoles which are destroyed almost immediately in acidic solutions.

The obtained crude product may be extracted in an organic solvent. It may also be crystallised in an organic or aqueous solvent resulting in an optically pure product, such as for instance one of the single enantiomers of a 2-(2-pyridinylmethylsulphinyl)-1H-benzimidazole in the neutral form. The acidic proton in the benzimidazole moiety may be abstracted by treating the crude product with a base such as NaOH followed by crystallisation of the formed salt in a solvent which may result in a product with an improved optical purity.

The invention is illustrated more in detail by the following examples.

EXAMPLES

Example 1

Asymmetric synthesis of (−)-5-methoxy-2-[[(4-methoxy-3,5-dimethyl-2-pyridinyl)-methyl]sulphinyl]-1 H-benzimidazole sodium salt, (−)-(Ia)-Na 59 g (180 mmol) of 5-methoxy-2-[[(4-methoxy-3,5-dimethyl-2-pyridinyl)-methyl]thio]-1H-benzimidazole was dissolved in 200 ml ethyl acetate. To the solution was added 0.3 ml (17 mmol) water. To the mixture was added 37 g (180 mmol) (+)-diethyl L-tartrate, 25 g (90 mmol) titanium(IV) isopropoxide and 16 ml (90 mmol) diisopropylethylamine at room temperature. The addition of 30 ml (160 mmol) cumene hydroperoxide (80%) was then performed over a period of 90 minutes at 34° C. After cooling to room temperature for 120 minutes a small sample of the mixture was taken for chiral and achiral chromatographic analyses. The mixture consisted of 82% sulphoxide with an enantiomeric excess (e.e.) of 87%. The mixture was diluted with 60 ml isooctane and 40 ml ethyl acetate whereupon the product was extracted three times with an aqueous ammonia (12%) solution with a total volume of 480 ml. The combined aqueous phases were neutrailsed by addition of 50 ml concentrated acetic acid. Thereafter, the workup procedure employed extraction, evaporation, sodium hydroxide addition and crystallisation procedures yielding 32.7 g of the title compound with a purity of 95.2% (achiral analysis) and with an enantiomeric excess (e.e.) of 99.8% (chiral analysis). The overall yield was 47.2%.

Example 2

Asymmetric synthesis of (+)-5-methoxy-2-[[(4-methoxy-3,5-dimethyl-2-pyridinyl)-methyl]sulphinyl]-1H-benzimidazole, (+)-(Ia)

Titanium(IV) isopropoxide (1.3 ml, 4.5 mmol) and water (41 μl, 2.3 mmol) were added with stirring to a solution of (+)-diethyl L-tartrate (1.5 ml, 9.0 mmol) dissolved in toluene (10 ml). The mixture was stirred for 20 minutes at room temperature and then 5-methoxy-2-[[(4-methoxy-3,5-dimethyl-2-pyridinyl)methyl]thio]-1H-benzimidazole (3.0 g, 9 mmol) and diisopropylethyl amine (0.45 ml, 2.6 mmol) were introduced. At 30° C. cumene hydroperoxide (tech, 80%, 1.8 ml, 9.9 mmol) was added. After 3 h at 30° C. the mixture consisted of 2.1% sulphide, 8.8% sulphone and 86.8% sulphoxide with an enantiomeric excess of 74%.

Example 3

Asymmetric synthesis of (+)-5-methoxy-2-[[(4-methoxy-3,5-dimethyl-2-pyridinyl)-methyl]sulphinyl]-1H-benzimidazole, (+)-(Ia).

To a mixture of (+)-diethyl L-tartrate (4.2 g, 20 mmol), titanium(IV) isopropoxide (2.9 g, 10 mmol) and ethyl acetate was added water (0.18 ml, 10 mmol). The solution was stirred for 20 minutes whereupon 5-methoxy-2-[[(4-methoxy-3,5-dimethyl-2-pyridinyl)-methyl]thio]-1H-benzimidazole (3,4 g, 10 mmol) was added together with KHCO₃ (0.31 g, 3.1 mmol) and cumene hydroperoxide (1.8 ml, 10 mmol). The addition was performed at room temperature. HPLC analysis was performed after 1.5 hours which showed 63.3% sulphoxide with an enantiomeric excess of 38.9%.

Example 4

Asymmetric synthesis of (−)-5-methoxy-2-[[(4-methoxy-3,5-dimethyl-2-pyridinyl)-methyl]sulphinyl]-1H-benzimidazole sodium salt, (−)-(Ia)-Na Water (0.45 ml, 25 mmol) was added at room temperature to a solution of (+)-diethyl L-tartrate (8.5 ml, 50 mmol) and titanium (IV) isopropoxide (7.4 ml, 25 mmol) in 250 ml methylene chloride. After 20 minutes 5-methoxy-2-[[(4-methoxy-3,5-dimethyl-2-pyridinyl)-methyl]thio]-1H-benzimidazole (8.2 g, 25 mmol) and diisopropylethylamine (1.3 ml, 7 mmol) were added and the solution was cooled to −20° C. After addition of cumene hydroperoxide (5.1 ml 80% soln, 28 mmol) the reaction mixture was kept at +2° C. for 66 h. Workup by addition of 2×125 ml sodium hydroxide solution was followed by neutralisation of the aqueous phase with ammonium chloride. Thereafter, the workup procedure employed extraction, evaporation, flash chromatography, sodium hydroxide addition and crystallisation procedures yielding 1.23 g (13.4%) g of the title compound with a an enantiomeric excess (e.e.) of 99.8% (chiral analysis).

Example 5

Asymmetric synthesis of (−)-5-methoxy-2-[[(4-methoxy-3,5-dimethyl-2-pyridinyl)-methyl]sulphinyl]-1H-benzimidazole, (−)-(Ia).

5-Methoxy-2-[[(4-methoxy-3,5-dimethyl-2-pyridinyl)methyl]-thio]-1H-benzimidazole (4.0 g, 12.1 mmol) was suspended in toluene (12 ml) (−)-Diethyl D-tartrate (0.17 ml, 1.0 mmol) and titanium(IV) isopropoxide (0.15 ml, 0.50 mmol) were added with stirring at 50° C. The mixture was stirred at 50° C. for 50 minutes and then N,N-diisopropylethylamine (0.085 ml, 0.50 mmol) was added at ca. 30° C. Then, cumene hydroperoxide (83%, 2.1 ml, 11.9 mmol) was added and the mixture was stirred for 15 minutes at 30° C. The crude mixture was shown to consist of 3.6% sulphide, 2.7% sulphone and 93% sulphoxide with an optical purity of 91% e.e. The product was not isolated.

Example 6

Asymmetric synthesis of (+)-5-methoxy-2-[[(4-methoxy-3,5-dimethyl-2-pyridinyl)-methyl]sulphinyl]-1H-benzimidazole, (+)-(Ia).

(+)-Diethyl L-tartrate (1.71 ml, 10 mmol) and titanium (IV) isopropoxide (1.5 ml, 5 mmol) were dissolved in methylene chloride (50 ml). Water (90 μl, 5 mmol) was added with stirring and the resultant mixture was heated to reflux for one hour. The mixture was cooled to room temperature. Thereafter, 5-methoxy-2-[[(4-methoxy-3,5-dimethyl-2-pyridinyl)methyl]thio]-1H-benzimidazole (1.65 g, 5 mmol) and cumene hydroperoxide (80%, 1.05 g, 5.5 mmol) were added at room temperature. The solution was stirred at room temperature for 90 minutes. The crude mixture was shown to consist of 42.8% sulphide, 4.1% sulphone and 48.3% sulphoxide with an optical purity of 43% e.e. The product was not isolated.

Example 7

Asymmetric synthesis of (+)-5-methoxy-2-[[(4-methoxy-3,5-dimethyl-2-pyridinyl)-methyl]sulphinyl]-1H-benzimidazole, (+)-(Ia).

5-Methoxy-2-[[(4-methoxy-3,5-dimethyl-2-pyridinyl)methyl]thio]-1H-benzimidazole (1.65 g, 5 mmol) was dissolved in methylene chloride (50 ml). (+)-Diethyl L-tartrate (1.71 ml, 10 mmol), titanium(IV) isopropoxide (1.5 ml, 5 mmol) and water (90 μl, 5 mmol) were added with stirring. The resultant mixture was stirred at room temperature for 20 minutes. Thereafter, cumene hydroperoxide (80%, 1.05 g, 5.5 mmol) were added at room temperature and the solution was stirred at room temperature for 90 minutes. The crude mixture was shown to consist of 38.9% sulphide, 8.4% sulphone and 47.6% sulphoxide with an optical purity of 32% e.e. The product was not isolated.

Example 8

Asymmetric synthesis of (+)-5-methoxy-2-[[(4-methoxy-3,5-dimethyl-2-pyridinyl)-methyl]sulphinyl]-1H-benzimidazole, (+)-(Ia).

5-Methoxy-2-[[(4-methoxy-3,5-dimethyl-2-pyridinyl)methyl]thio]-1H-benzimidazole (0.5 g, 1.5 mmol) was suspended in toluene (2.5 ml). Water 9.2 μl (0.5 mmol), (+)-Diethyl L-tartrate (0.39 ml, 2.3 mmol) and titanium(IV) isopropoxide (0.27 ml, 0.91 mmol) were added at 50° C. The mixture was warmed at 50° C. for 90 minutes whereupon 0.25 ml of the solution was transferred to a test-tube. To this tube was then added 25 μl of cumene hydroperoxide (80%) and almost immediately thereafter this mixture consisted of 41% desired sulphoxide with an optical purity of 69.5% ee. The product was not isolated.

Example 9

Asymmetric synthesis of (−)-5-methoxy-2-[[(4-methoxy-3,5-dimethyl-2-pyridinyl)-methyl]sulphinyl]-1H-benzimidazole sodium salt, (−)-(Ia)-Na 1.6 kg (5.0 mol) of 5-methoxy-2-[[(4-methoxy-3,5-dimethyl-2-pyridinyl)-methyl]thio]-1H-benzimidazole was dissolved in 7.5 l ethyl acetate. To the solution was added 31 ml (1.7 mol) water. To the mixture was added 860 ml (5.0 mol) (+)-diethyl L-tartrate, 740 ml (2.5 mol) titanium(IV) isopropoxide and 430 ml (2.5 mol) diisopropylethylamine at room temperature. The addition of 830 ml (4.5 mol) cumene hydroperoxide (80%) was then performed over a period of 50 minutes at 30° C. After an additional hour at 30° C. the reaction was completed. Chiral and achiral chromatographic analyses show that the mixture consists of 75% sulphoxide with an enantiomeric excess (e.e.) of 80%, 19% unreacted sulphide and 3.8% sulphone. The mixture was cooled to 10° C. and after addition of 1.5 l isooctane and 0.5 l ethyl acetate, the product was extracted three times with an aqueous ammonia (12%) solution with a total volume of 14 l. The combined aqueous phases were neutralised by addition of 1.5 l concentrated acetic acid.

Thereafter, the workup procedure employed extraction, evaporation, sodium hydroxide addition and crystallisation procedures yielding 0.80 kg of the title compound with a purity of 99.3% (achiral analysis) and with an enantiomeric excess (e.e.) of 99.8% (chiral analysis).The overall yield was 44%.

Example 10

Asymmetric synthesis of (+)-5-methoxy-2-[[(4-methoxy-3,5-dimethyl-2-pyridinyl)-methyl]sulphinyl]-1 H-benzimidazole sodium salt, (+)-(Ia)-Na 1.6 kg (5.0 mol) of 5-methoxy-2-[[(4-methoxy-3,5-dimethyl-2-pyridinyl)- methyl]thio]-1H-benzimidazole was dissolved in 6.1 l ethyl acetate. To the solution was added 31 ml (1.7 mol) water. To the mixture was added 860 ml (5.0 mol) (−)-diethyl D-tartrate, 740 ml (2.5 mol) titanium(IV) isopropoxide and 430 ml (2.5 mol) diisopropylethylamine at room temperature. The addition of 830 ml (4.5 mol) cumene hydroperoxide (80%) was then performed over a period of 25 minutes at 30° C. After additional 30 minutes at 30° C. the reaction was completed. Chiral and achiral chromatographic analyses show that the mixture consists of 71% sulphoxide with an enantiomeric excess (e,e.) of 73%. The mixture was cooled to 10° C. and after addition of 1.7 l isooctane, the product was extracted three times with an aqueous ammonia (12%) solution with a total volume of 14 l. The combined aqueous phases were neutralised by addition of 1.5 l concentrated acetic acid. Thereafter, the workup procedure employed extraction, evaporation, sodium hydroxide addition and crystallisation procedures yielding 0.45 kg of the title compound with a purity of 99.9% (achiral analysis) and with an enantiomeric excess (e.e.) of 99.8% (chiral analysis). The overall yield was 24.6%.

Example 11

Asymmetric synthesis of (+)-5-methoxy-2-[[(4-methoxy-3,5-dimethyl-2-pyridinyl)-methyl]sulphinyl]-1 H-benzimidazole sodium salt, (+)-(Ia).

6.2 kg (18.8 mol) Methoxy-2-[[(4-methoxy-3,5-dimethyl-2-pyridinyl)methyl]thio]-1H-benzimidazole in toluene suspension (25 l) was heated to 54° C. Water (44 ml, 2.4 mol), (−)-diethyl D-tartrate (2.35 kg, 11.4 mol) and titanium(IV) isopropoxide (1.60 kg, 5.6 mol) were added with stirring and then the mixture was stirred at 54° C. for 50 minutes. The temperature was adjusted to 30° C. whereupon N,N-diisopropylethylamine (720 g, 5.6 mol) was added to the solution. Then, cumene hydroperoxide (83.5%, 3.30 kg, 18.2 mol) was added and the mixture was stirred for one hour at 30° C. The crude mixture was shown to consist of 7% sulphide, 1.2% sulphone and 90.6% sulphoxide with an optical purity of 94.3% e.e. Aqueous ammonia (12.5%, 20 l) was added. The solution was extracted three times with aqueous ammonia (3×20 l). To the combined aqueous layers was added methyl isobutyl ketone (9 l). The aqueous layer was pH-adjusted with acetic acid and then the layers were separated. The aqueous layer was extracted with an additional portion of methyl isobutyl ketone (9 l).To make the sodium salt, to the solution was added an aqueous solution of NaOH (49.6%, 1.07 kg, 13.2 mol) and acetonitrile (70 l). The solution was concentrated and the product started to crystallize. 3.83 kg of the (+)-enantiomer of the sodium salt of omeprazole was isolated with an optical purity of 99.6% e.e.

Example 12

Asymmetric synthesis of (+)-5-fluoro-2-[[(4-cydopropylmethoxy-2-pyridinyl)methyl]sulphinyl]-1 H-benzimidazole, (+)-(Ib)

Titanium (IV) isopropoxide (8.9 ml, 30 mmol) and water (0.54 ml, 30 mmol) was added with stirring to a mixture of (+)-diethyl L-tartrate (10.3 ml, 60 mmol) and methylene chloride (60 ml). The solution was stirred for 30 minutes at room temperature and then 5-fluoro-2-[[(4-cyclopropylmethoxy-2-pyridinyl)methylthio]-1 H-benzimidazole (9.9 g, 30 mmol) and diisopropylethylamine (1.50 ml, 8.7 mmol) were introduced. At room temperature cumene hydroperoxide (tech, 80%, 6.0 ml, 33 mmol) was added. After 3 h at room temperature the mixture consisted of a crude sulphoxide with an enantiomeric excess (e.e.) of 60%. After purification on silica gel with methanol/methylene chloride as eluent followed by repeated crystallisations from ethanol there was obtained 1.1 g (11%) of the title compound with an enantiomeric excess of 98.6%.

Example 13

Asymmetric synthesis of (−)-5-fluoro-2-[[(4-cyclopropylmethoxy-2-pyridinyl)methyl]sulphinyl]-1H-benzimidazole, (−)-(Ib).

5-Fluoro-2-[[(4-cyclopropylmethoxy-2-pyridinyl)methyl]thio]-1H-benzimidazole (15.0 g, 45 mmol) was suspended in toluene (60 ml). Water (34 $\mu$l, 1.9 mmol), (−)-diethyl D-tartrate (1.60 ml, 9.3 mmol) and titanium(IV) isopropoxide (1.3 ml, 4.5 mmol) were added with stirring at 50° C. The mixture was stirred at 40° C. for 50 minutes and then N,N-diisopropylethylamine (0.79 ml, 4.5 mmol) was added. The temperature was adjusted to 35° C. and then cumene hydroperoxide (83%, 8.1 ml, 45 mmol) was added. The mixture was stirred for 30 minutes at 35° C. The crude mixture was shown to consist of 6.5% sulphide, 2.7% sulphone and 90% sulphoxide with an optical purity of 87.7% e.e. The product started to crystallize during the oxidation and was isolated from the reaction mixture by filtration. There was obtained 11.7 g of the desired product with an optical purity of 98.8% e.e. The material was also shown to consist of 2.2% sulphide and 0.9% of sulphone. Yield: 71.2%.

Example 14

Asymmetric synthesis of (−)-5-fluoro-2-[[(4-cyclopropylmethoxy-2-pyridinyl)methyl]sulphinyl]-1 H-benzimidazole, (−)-(Ib).

5.0 g (15 mmol) of 5-fluoro-2-[[(4-cyclopropylmethoxy-2-pyridinyl)methyl]-thio]-1H-benzimidazole was mixed with toluene (30 ml). To the mixture was added 32 $\mu$l (1.8 mmol) of water, 1.3 ml (7.6 mmol) of (−)-diethyl D-tartrate and 0.90 ml (3.0 mmol) of titanium(IV) isopropoxide. The mixture was stirred for 60 minutes at 50° C. and then cooled 30° C. Thereafter, 2.8 ml (15 mmol) of cumene hydroperoxide (80%) was added to the solution. The mixture was stirred for one hour at 30° C. and thereafter cooled to 0° C. To the mixture, ethyl acetate (20 ml) was added and the resultant solution was extracted three times with an aqueous ammonia (12%) solution with a total volume of 60 ml. The combined aqueous layers were neutralized by the addition of 17 ml of concentrated acetic acid and thereafter extracted with ethyl acetate (4×60 ml). The organic layer was dried over magnesium sulphate and then removed to give a crude product with an optical purity of 59% ee. The residue, as an oil, (3.2 g) was dissolved in acetone (8 ml). A formed precipitate was filtered off. There was obtained 1.6 g of a crude produced of the desired compound as a white solid. The optical purity was shown to be 87% ee.

Example 15

Asymmetric synthesis of (+)-5-fluoro-2-[[(4-cyclopropylmethoxy-2-pyridinyl)methyl]sulphinyl]-1H-benzimidazole, (+)-(Ib).

5-Fluoro-2-[[(4-cyclopropylmethoxy-2-pyridinyl)methyl]thio]-1H-benzimidazole (3.6 kg, 10.9 mol) was suspended in toluene (15 l). Water (8.9 ml, 0.49 mol), (+)-diethyl L-tartrate (460 g, 2.2 mol) and titanium(IV) isopropoxide (310 g, 1.09 mol) were added with stirring at 40° C. The mixture was stirred at 40° C. for 50 minutes and then N,N-diisopropyl-ethylamine (190 ml, 1.09 mol) was added. The temperature was adjusted to 30° C. and then cumene hydroperoxide (83%, 2.0 kg, 11 mol) was added and the oxidation was completed within 30 minutes. The crude mixture was shown to consist of 8.9% sulphide, 3.3% sulphone and 87% sulphoxide with an optical purity of 86% e.e. The product started to crystallize during the oxidation and was isolated from the reaction mixture by filtration. There was obtained 2.68 kg of the product with an optical purity of 96% e.e. The material was also shown to consist of 2.3% sulphide and 1.7% sulphone. The product was recrystallized in methanol/toluene. There was obtained 1.66 kg (yield: 44%) of the desired product with an optical purity of 99.7%. The content of sulphide and sulphone was less than 0.1% and 0.3% respectively.

Example 16

Asymmetric synthesis of (−)-5-fluoro-2-[[(4-cyclopropylmethoxy-2-pyridinyl)methyl]sulphinyl]-1H-benzimidazole, (−)-(Ib).

5-Fluoro-2-[[(4-cyclopropylmethoxy-2-pyridinyl)methyl]thio]-1H-benzimidazole (3.6 kg, 10.9 mol) was suspended in toluene (14.4 l). Water (10 ml, 0.55 mol), (−)-diethyl D-tartrate (460 g, 2.2 mol) and titanium(IV) isopropoxide (310 g, 1.10 mol) were added with stirring at 40° C. The mixture was stirred at 40° C. for 50 minutes and then N,N-diisopropyl-ethylamine (190 ml, 1.1 mol) was added. The temperature was adjusted to 35° C. and then cumene hydroperoxide (83%, 2.0 kg, 11 mol) was added. The mixture was stirred for one hour at 35° C. The crude mixture was shown to consist of 8.7% sulphide, 4.8% sulphone and 85% sulphoxide with an optical purity of 78% e.e. The product started to crystallize during the oxidation and was isolated from the reaction mixture by filtration. There was obtained 2.78 kg of the product with an optical purity of 97% e.e. The material was also shown to consist of 1.9% sulphide and 2.5% sulphone. The product was recrystallized in methanol/toluene. There was obtained 1.67 kg (yield: 44%) of the desired product as off white crystals, 99.8% (e.e.). The content of sulphide and sulphone was less than 0.1% and 0.6%, respectively.

Example 17

Asymmetric synthesis of (+)-5-carbomethoxy-6-methyl-2-[[(3,4-dimethoxy-2-pyridinyl)methyl]sulphinyl]-1H-benzimidazole, (+)-(Ic).

3.4 g (9.1 mmol) of 5-carbomethoxy-6-methyl-2-[[(3,4-dimethoxy-2-pyridinyl)methyl]thio]-1H-benzimidazole was suspended in toluene (20 ml). To the mixture was added 41 μl (2.3 mmol) of water, 1.7 ml (10 mmol) of (+)-diethyl L-tartrate and 1.3 g (4.6 mmol) of titanium(IV) isopropoxide. The mixture was stirred for 60 minutes at 50° C. and then 0.78 ml (4.5 mmol) of N,N-diisopropylethylamine was added. The mixture was cooled to 30° C. and toluene (10 ml) was added. To the mixture was then added 1.7 ml (80%, 9.2 mmol) of cumene hydroperoxide. After a few minutes, more toluene (70 ml) was added and after one hour at 30° C., the mixture consisted of 12.5% sulphide, 3.5% sulphone and 84% sulphoxide with an optical purity of 95.6% e.e. The mixture was cooled to room temperature and a formed precipitate was filtered off. There was obtained 2.5 g of a crude product of the desired compound as a solid which was shown to have an optical purity of 98.2% e.e.

Example 18

Asymmetric synthesis of (−)-5-carbomethoxy-6-methyl-2-[[(3,4-dimethoxy-2-pyridinyl)methyl]sulphinyl]-1H-benzimidazole, (−)-(Ic)

Titanium (IV) isopropoxide (7.5 ml, 25 mmol) and water (0.45 ml, 25 mmol) were added with stirring to a mixture of (−)-diethyl D-tartrate (8.6 ml, 50 mmol) and methylene chloride (50 ml). The solution was stirred for 30 minutes at room temperature and then 5-carbomethoxy-6-methyl-2-[[(3,4-dimethoxy-2-pyridinyl)methyl]thio]-1-H-benzimidazole (9.3 g, 25 mmol) and diisopropylethylamine (1.25 ml, 7.2 mmol) were introduced. At room temperature cumene hydroperoxide (tech, 80%, 5.1 ml, 27 mmol) was added and reacted for 3 h at room temperature. The crude product consisted of a crude sulphoxide with an enantiomeric excess (e.e.) of 71%. After purification on silica gel with methanol/methylene chloride as eluent followed by repeated crystallisations from ethanol there was obtained 2.9 g (30%) of the title compound with an enantiomeric excess of 99.4%.

Example 19

Asymmetric synthesis of (−)-5-carbomethoxy-6-methyl-2-[[(3,4-dimethoxy-2-pyridinyl)methyl]sulphinyl]-1H-benzimidazole, (−)-(Ic).

4.7 g (12.5 mmol) of 5-carbomethoxy-6-methyl-2-[[(3,4-dimethoxy-2-pyridinyl)methyl]thio]-1H-benzimidazole was dissolved in methylene chloride (100 ml). To the solution was added 80 μl (4.5 mmol) of water, 3.2 ml (19 mmol) of (−)-diethyl D-tartrate and 2.2 ml (7.5 mmol) of titanium(IV) isopropoxide. The mixture was stirred for 60 minutes at reflux and then cooled to room temperature. 0.88 ml (5.0 mmol) of N,N-diisopropylethylamine was added and the mixture was then stirred for 30 minutes. 2.15 ml (12 mmol) cumene hydroperoxide (80%) was added and after 2 h at room temperature the mixture consisted of 23% sulphide and 72% sulphoxide with an optical purity of 88% e.e. To the mixture, methylene chloride (100 ml) was added and the resultant solution was extracted three times with an aqueous ammonia (12%) solution with a total volume of 300 ml. The combined aqueous layers were neutralized by the addition of 50 ml of concentrated acetic acid, after which white crystals started to precipitate. The crystals was filtered off, washed with diethyl ether and dried to give 2.34 g (48%) white crystals of the title compound consisted of 1.5% sulphide and 1.8% sulphone with an optical purity of 92% e.e.

Example 20

Asymmetric synthesis of (+)-5-carbomethoxy-6-methyl-2-[[(3,4-dimethoxy-2-pyridinyl)methyl]sulphinyl]-1H-benzimidazole, (+)-(Ic).

4.7 g (12.5 mmol) of 5-carbomethoxy-6-methyl-2-[[(3,4-dimethoxy-2-pyridinyl)methyl]thio]-1H-benzimidazole was dissolved in methylene chloride (100 ml). To the solution was added 80 μl (4.5 mmol) of water, 3.2 ml (19 mmol) of (+)-diethyl L-tartrate and 2.2 ml (7.5 mmol) of titanium(IV) isopropoxide. The mixture was stirred for 60 minutes at reflux and then cooled to room temperature. 1.1 ml (6.3 mmol) of N,N-diisopropylethylamine was added and the mixture was then stirred for 30 minutes. 2.15 ml (12 mmol) cumene hydroperoxide (80%) was added and after 2 h at room temperature the mixture consisted of 19% sulphide and 77% sulphoxide with an optical purity of 90% e.e. To the mixture, methylene chloride (100 ml) was added and the resultant solution was extracted three times with an aqueous ammonia (12%) solution with a total volume of 300 ml. The combined aqueous layers were neutralized by the addition of concentrated acetic acid (50 ml) which afforded white crystals. The crystals were filtered off, washed with diethyl ether and dried to give 3.29 g (68%) of white crystals of the title compound with an optical purity of 93% e.e. The material also consisted of 2.2% sulphide and 0.9% sulphone.

Example 21

Asymmetric synthesis of (−)-2-[[[3-methyl-4-(2,2,2-trifluoroethoxy)-2-pyridinyl]methyl]sulphinyl]-1H-benzimidazole, (−)-(Id).

2.1 g (6.0 mmol) of 2-[[[3-methyl-4-(2,2,2-trifluoroethoxy)-2-pyridinyl]-methyl]thio]-1H-benzimidazole was dissolved in toluene (50 ml). To the solution was added 65 μl (3.6 mmol) of water, 2.6 ml (15.0 mmol) of (−)-diethyl D-tartrate and 1.8 ml (6.0 mmol) of titanium(IV) isopropoxide. The mixture was stirred for 60 minutes at 50° C. and then cooled to room temperature. 1.05 ml (6.0 mmol) of N,N-diisopropylethylamine and 1.1 ml (6.0 mmol) of cumene hydroperoxide (80%) were added. After stirring for 16 h at room temperature the mixture consisted of 11% sulphide, 7% sulphone and 78% sulphoxide according to achiral HPLC. To the mixture 50 ml toluene was added and the resultant solution was extracted three times with an aqueous ammonia (12%) solution with a total volume of 150 ml. The combined aqueous layers were neutralized by the addition of concentrated acetic acid (30 ml). Thereafter, the workup procedure employed extraction, evaporation and flash chromatography yielding 1.2 g of the title compound with a purity of 99.9% (achiral analysis) and with an enantiomeric excess (e.e.) of 55% (chiral analysis). After treating the residue with acetonitrile there was obtained a precipitate that was removed by filtration. Evaporation of the filtrate afforded an oil with enhanced optical purity. Repeating this procedure a couple of times afforded 0.63 g (29%) of the desired compound as an oil with an optical purity of 99.5% e.e.

Example 22

Asymmetric synthesis of (+)-2-[[[3-methyl-4-(2,2,2-trifluoroethoxy)-2-pyridinyl]methyl]sulphinyl]-1H-benzimidazole, (+)-(Id).

2.1 g (6.0 mmol) of 2-[[[3-methyl-4-(2,2,2-trifluoroethoxy)-2-pyridinyl]-methyl]thio]-1H-benzimidazole was dissolved in 50 ml of toluene. To the solution was added 65 μl (3.6 mmol) of water, 2.6 ml (15.0 mmol) of (+)-diethyl L-tartrate and 1.8 ml (6.0 mmol) of titanium(IV) isopropoxide. The mixture was stirred for 60 minutes at 50° C. and then cooled to room temperature. 1.05 ml (6.0 mmol) of N,N-diisopropylethylamine and 1.1 ml (6.0 mmol) of cumene hydroperoxide (80%) were added. After stirring for 16 h at room temperature the mixture consisted of 13% sulphide, 8% sulphone and 76% sulphoxide according to achiral HPLC. To the mixture toluene (50 ml) was added and the resultant solution was extracted three times with an aqueous ammonia (12%) solution with a total volume of 150 ml. The combined aqueous layers were neutralized by the addition of concentrated acetic acid (30 ml). Thereafter, the workup procedure employed extraction, evaporation and flash chromatography yielding 0.85 g of the title compound with a purity of 99.9% (achiral analysis) and with an enantiomeric excess (e.e.) of 46% (chiral analysis). After treating the residue with acetonitrile there was obtained a precipitate that was removed by filtration. Evaporation of the filtrate afforded an oil with enhanced optical purity. Repeating this procedure a couple of times afforded 0.31 g (14%) of the desired compound as an oil with an optical purity of 99.6% e.e.

Example 23

Asymmetric synthesis of (−)-5-difluoromethoxy-2-[[(3,4-dimethoxy-2-pyridinyl)methyl]sulphinyl]-1H-benzimidazole, (−)-(Ie).

1.1 g (3.0 mmol) of 5-difluoromethoxy-2-[[(3,4-dimethoxy-2-pyridinyl)methyl]thio]-1H-benzimidazole was dissolved in methylene chloride (25 ml). To the solution were added 20 μl (1.1 mmol) of water, 0.81 ml (4.7 mmol) of (−)-diethyl D-tartrate and 0.56 ml (1.9 mmol) of titanium (IV) isopropoxide. The mixture was stirred for 60 minutes at reflux and then cooled to room temperature. Thereafter, 0.22 ml (1.3 mmol) of N,N-diisopropylethylamine was added followed by the addition of 0.57 ml (80%, 3.1 mmol) cumene hydroperoxide (80%). After 21 h at room temperature the mixture consisted of 10% sulphide and 89% sulphoxide with an optical purity of 86% e.e. To the mixture, methylene chloride (25 ml) was added and the resultant solution was extracted three times with an aqueous ammonia (12%) solution with a total volume of 300 ml. The combined aqueous layers were neutralized by the addition of 25 ml of concentrated acetic acid and thereafter extracted with methylene chloride (3×100 ml). The residue, as an oil, (1.16 g) was dissolved in hot acetonitrile (20 ml). A white precipitate was formed when the solution was cooled to room temperature and there was obtained 0.35 g (29%) of the desired compound by filtration. There was also obtained 0.71 g of the desired compound with a lower optical purity from the filtrate by evaporation thereof. The optical purity of the crystals and the filtrate was shown to be 97.4% e.e. and 75% ee. respectively.

Example 24

Asymmetric synthesis of (+)-5-difluoromethoxy-2-[[(3,4-dimethoxy-2-pyridinyl)methyl]sulphinyl]-1H-benzimidazole, (+)-(Ie).

1.1 g (3.0 mmol) of 5-difluoromethoxy-2-[[(3,4-dimethoxy-2-pyridinyl)methyl]thio]-1H-benzimidazole was dissolved in methylene chloride (25 ml). To the solution were added 20 μl (1.1 mmol) of water, 0.81 ml (4.7 mmol) of (+)-diethyl L-tartrate and 0.56 ml (1.9 mmol) of titanium (IV) isopropoxide. The mixture was stirred for 60 minutes at reflux and then cooled to room temperature. Thereafter, 0.22 ml (1.3 mmol) of N,N-diisopropylethylamine was added followed by the addition of 0.57 ml (80%, 3.1 mmol) cumene hydroperoxide (80%). After 21 h at room temperature the mixture consisted of 8% sulphide and 92% sulphoxide with an optical purity of 87% e.e. To the mixture, methylene chloride (25 ml) was added and the resultant solution was extracted three times with an aqueous ammonia (12%) solution with a total volume of 300 ml. The combined aqueous layers were neutralized by the addition of 25 ml of concentrated acetic acid and thereafter extracted with methylene chloride (3×100 ml). The solvent was removed and the residue, as an oil, (0.86 g) was dissolved in hot acetonitrile (20 ml). A white precipitate was formed when the solution was cooled to room temperature and there was obtained 0.36 g (30%) of the desired compound by filtration. There was also obtained 0.48 g of the desired compound with a lower optical purity from the filtrate by evaporation thereof. The optical purity of the crystals and the filtrate was shown to be 97.4% e.e. and 78% ee. respectively.

Example 25

Asymmetric synthesis of (−)-2-[[[4-(3-methoxypropoxy)-3-methyl-2-pyridinyl]methyl]sulphinyl]-1H-benzimidazole, (−)-(If).

2.1 g (6.3 mmol) of 2-[[[4-(3-methoxypropoxy)-3-methyl-2-pyridinyl]methyl]thio]-1H-benzimidazole was dissolved in 50 ml of toluene. To the solution was added 40 μl (2.2 mmol) of water, 1.6 ml (9.4 mmol) of (−)-diethyl D-tartrate and 1.1 ml (3.8 mmol) of titanium(IV) isopropoxide. The mixture was stirred for 60 minutes at 50° C. and then cooled to room temperature. 0.44 ml (2.6 mmol) of N,N-diisopropylethylamine and 1.1 ml (6.0 mmol) of cumene hydroperoxide (80%) were added. After stirring for 2 h at room temperature the mixture consisted of 9% sulphide, 4% sulphone and 86% sulphoxide according to achiral HPLC. To the mixture toluene (50 ml) was added and the resultant solution was extracted three times with an aqueous ammonia (12%) solution with a total volume of 150 ml. The combined aqueous layers were neutralized by the addition of concentrated acetic acid (30 ml). Thereafter, the workup procedure employed extraction, evaporation and flash chromatography yielding 1.62 g of the title compound with a purity of 99.9% (achiral analysis) and with an enantiomeric excess (e.e.) of 90% (chiral analysis). After treating the material with acetonitrile there was a precipitate that could be removed by filtration. Concentrating the filtrate afforded 1.36 g (60%) of the title compound as an oil with an optical purity of 91.5% e.e.

Example 26

Asymmetric synthesis of (+)-2-[[[4-(3-methoxypropoxy)-3-methyl-2-pyridinyl]methyl]sulphinyl]-1H-benzimidazole, (+)-(If).

2.1 g (6.3 mmol) of 2-[[[4-(3-methoxypropoxy)-3-methyl-2-pyridinyl]methyl]thio]-1H-benzimidazole was dissolved in 50 ml of toluene. To the solution was added 40 μl (2.2 mmol) of water, 1.6 ml (9.4 mmol) of (+)-diethyl L-tartrate and 1.1 ml (3.8 mmol) of titanium(IV) isopropoxide. The mixture was stirred for 60 minutes at 50° C. and then cooled to room temperature. 0.44 ml (2.6 mmol) of N,N-diisopropylethylamine and 1.1 ml (6.0 mmol) of cumene hydroperoxide (80%) were added to the solution. After stirring for 2 h at room temperature the mixture consisted of 9% sulphide, 4% sulphone and 85% sulphoxide according to HPLC. To the mixture toluene (50 ml) was added and the resultant solution was extracted three times with an aqueous ammonia (12%) solution with a total volume of 150 ml. The combined aqueous layers were neutralized by the addition of concentrated acetic acid (30 ml). Thereafter, the workup procedure employed extraction, evaporation and flash chromatography yielding 1.63 g of the title compound with a purity of 99.9% (achiral analysis) and with an enantiomeric excess (e.e.) of 91% (chiral analysis). After treating the material with acetonitrile, there was a precipitate that could be removed by filtration. Concentrating the filtrate afforded 1.1 g (49%) of the title compound as an oil with an optical purity of 96.0% e.e.

Example 27

Asymmetric synthesis of (−)-2-[2-(N-isobutyl-N-methylamino)benzylsulphinyl]benzimidazole, (−)-(Ig).

2.0 g (6.1 mmol) of 2-[2-(N-isobutyl-N-methylamino) benzylthio]-benzimidazole was dissolved in toluene (6 ml). While stirring, 40 μl (2.2 mol) of water, 1.6 ml (9.3 mmol) of (+)-diethyl L-tartrate and 1.1 ml (3.7 mmol) of titanium (IV) isopropoxide were added at 50° C. The resulting mixture was stirred at 50° C. for 1 hour and then 0.53 ml (3.0 mmol) of N,N-diisopropylethylamine was added. The reaction mixture was then cooled to 30° C. whereupon 1.1 ml (6.1 mmol) of cumene hydroperoxide (80%) was added. The mixture was stirred at 30° C. for 50 min. Analysis of the reaction mixture indicated that the optical purity of the formed sulphoxide was 92% e.e. The mixture was cooled to room temperature and diluted with small amount of methylene chloride. Column chromatography [silica gel, eluted with 4% MeOH/CH$_2$Cl$_2$(NH$_3$ saturated)] yielded an oil which was re-chromatographed (silica gel, eluted with 20% EtOAc/hexane). The obtained (1.6 g) crude product, as an oil was treated with a small amount of acetonitrile in order to enhance the optical purity. A formed precipitate (270 mg) was removed by filtration. The solvent of the filtrate was removed yielding 1.2 g of the desired compound as an oil. The optical purity of the material was 96% e.e.

Example 28

Asymmetric synthesis of (+)-2-[2-(N-isobutyl-N-methylamino)benzylsulphinyl]benzimidazole, (+)-(Ig).

2.0 g (6.1 mmol) of 2-[2-(N-isobutyl-N-methylamino) benzylthio]-benzimidazole was dissolved in toluene (6 ml). While stirring, 40 μl (2.2 mmol) of water, 1.6 ml (9.3 mmol) of (−)-diethyl D-tartrate and 1.1 ml (3.7 mmol) of titanium (IV) isopropoxide were added at 50° C. The resulting mixture was stirred at 50° C. for 1 hour and then 0.53 ml (3.0 mmol) of N,N-diisopropylethylamine was added. The reaction mixture was then cooled to 30° C. whereupon 1.1 ml (6.1 mmol) of cumene hydroperoxide (80%) was added. The mixture was stirred at 30° C. for 50 min. Analysis of the reaction mixture indicated that the optical purity of the formed sulphoxide was 91% e.e. The mixture was cooled to room temperature and diluted with small amount of methylene chloride. Column chromatography [silica gel, eluted with 4% MeOH/CH$_2$Cl$_2$(NH$_3$ saturated)] yielded crude product as an oil. This material was treated with a mixture of ethyl acetate and hexane (10% EtOAc). A formed precipitate (140 mg) was removed by filtration. The solvent of the filtrate was removed yielding 0.95 g of the desired compound as an oil. The optical purity of the material was 96% e.e Example 29

Asymmetric synthesis of two of the stereoisomers of 2-[(4-methoxy-6,7,8,9-tetrahydro-5H-cyclohepta[b]pyridin-9-yl)sulphinyl]-1H-benzimidazole, (Ih).

In the following example, the first diastereomer of the title compound eluted on straight phase (silica gel) is named diastereomer A and second as diastereomer B.

Synthesis: 0.51 g (1.57 mmol) of the racemate of 2-[(4-methoxy-6,7,8,9-tetrahydro-5H-cyclohepta[b]-pyridin-9-yl)thio]-1H-benzimidazole was suspended in 20 ml of toluene. Under stirring at room temperature, 0.34 g (1.6 mmol) of (+)-diethyl L-tartrate, 71 μl (0.4 mmol) of water and 0.22 g (0.78 mmol) of titanium (IV) isopropoxide were added. The mixture was stirred at 50° C. for 50 minutes and then 100 mg (0.78 mmol) of N,N-diisopropylethylamine was added at room temperature. The addition of 0.33 g (160 mmol) cumene hydroperoxide (80%) was then performed over a period of 5 minutes at room temperature whereupon the solution was stirred at room temperature for 24 hours. The stereoisomeric composition of the title compound in the crude mixture was as follows; The ratio of diastereomers was 4:3 in favour of diastereomer A. The optical purity of the (-)-enantiomer of diastereomer A was 76% e.e. and the optical purity of the (+)-enantiomer of diastereomer B was 68% e.e. The product mixture was washed with water (3×25 ml) dried over Na$_2$SO$_4$ and the solvent removed. Flash chromatography of the residue (methanol-methylene chloride 0 to 5%) yielded 0.25 g (47%) of the enantiomeric enriched diastereomeric sulphoxide as a syrup.

Separation of the diastereomers. A repeated chromatographic preparation (methanol-methylene chloride 0 to 5%) afforded a separation of the two diastereomers. Thus, the (-)-enantiomer of diastereomer A was obtained as a syrup (0.14 g) with an optical purity of 77% e.e. The (+)-enantiomer of diastereomer B was also obtained as a syrup (0.085 g) with an optical purity of 68% e.e., however, diastereomer B was contaminated with ca. 10% of diastereomer A.

Optical purification: The optical purity of the (-)-enantiomer of diastereomer A was enhanced by the addition of ca. 2 ml of acetonitrile to the enantiomerically enriched preparation of diastereomer A (0.14 g). After stirring over night, the formed precipitate (almost racemic diastereomer A) was filtered off and the solvent of the filtrate was removed by film evaporation. Thus, there was obtained 85 mg of the (-)-enantiomer of diastereomer A as a syrup with an optical purity of 88% e.e. The optical purity of the (+)-enantiomer of the diastereomer B was enhanced in a similar way. Thus, by addition of acetonitrile (2 ml) to the enantiomerically enriched preparation of diastereomer B (0.085 g) followed by stirring over night resulted in a precipitate which was filtered off. There was obtained 0.050 g of the (+)-enantiomer of diastereomer B with an optical purity of 95% e.e.

The best mode to carry out the present invention known at present is as described in Example 11.

Reference Example A

Oxidation of 5-methoxy-2-[[(4-methoxy-3,5-dimethyl-2-pyridinyl)methyl]thio]-1H-benzimidazole using tert-butyl hydroperoxide under neutral conditions. (The method used is in accordance with the method used in Euro. J. Biochem. 166 (1987) 453–459 and described in J. Am. Chem. Soc. 106 (1984) 8188).

Water (90 μl, 5 mmol) was added at room temperature to a solution of (+)-diethyl L-tartrate (1.7 ml, 10 mmol) and titanium (IV) isopropoxide (1.5 ml, 5 mmol) in 50 ml methylene chloride. After 20 minutes 5-methoxy-2-[[(4-methoxy-3,5-dimethyl-2-pyridinyl)methyl]thio]-1H-benzimidazole (6.6 g, 5 mmol) was dissolved in the reaction mixture and the solution was cooled to −20° C. A 3 M solution of tert-butyl hydroperoxide in toluene (1.8 ml, 5.5 mmol) was added and the mixture was kept at −20° C. for 120 h. After this time the mixture consisted of 28% of sulphide (starting material), 8.6% sulphone, 30.6% (−)-enantiomer of sulphoxide and 28.1% (+)-enantiomer of sulphoxide (i.e. ee=4%). In a similar experiment run at +8° C. for 7 h the mixture consisted of 32.4% of sulphide, 8.7% sulphone, 24.6% (−)-enantiomer of sulphoxide and 26.7% (+)-enantiomer of sulphoxide (i.e. ee=4%).

Reference Example B

Oxidation of 5-methoxy-2-[[(4-methoxy-3,5-dimethyl-2-pyridinyl)methyl]thio]-1H-benzimidazole using cumene hydroperoxide at −22° C. without addition of a base. (The oxidation method used is described in Tetrahedron (1987), 43, 5135.)

The experiment was performed using the same conditions as in Reference A with the exception that cumene hydroperoxide was used instead of tert-butyl hydroperoxide. After 120 at −22° C. the mixture consisted of 29% sulphide, 3.8% sulphone, 29.1% (−)enantiomer of sulphoxide and 35.5% (+)-enantiomer of sulphoxide (i.e. ee=10%).

Reference Example C

Oxidation of 5-methoxy-2-[[(4-methoxy-3,5-dimethyl-2-pyridinyl)methyl]thio]-1H-benzimidazole using cumene hydroperoxide under neutral conditions.

Water (450 μl, 25 mmol) was added at room temperature to a solution of (+)-diethyl L-tartrate (8.5 ml, 50 mmol) and titanium (IV) isopropoxide (7.4 ml, 25 mmol) in 50 ml methylene chloride. After 20 minutes 5-methoxy-2-[[(4-methoxy-3,5-dimethyl-2-pyridinyl)methyl]thio]-1H-benzimidazole (8.2 g, 25 mmol) was added and the mixture was divided in 3 portions. To one of the portions cumene hydroperoxide (1.7 ml 80% soln, 9.2 mmol) was added at room temperature, and a sample was removed after 3 h and 20 minutes. The mixture consisted of 29.4% sulphide, 6.3% sulphone, 22.0% (−)-enantiomer of sulphoxide and 35% (+)-enatiomer of sulphoxide (ii.e. ee=23%).

Reference Example D

Oxidation of 5-methoxy-2-[[(4-methoxy-3.5-dimethyl-2-pyridinyl)methyl]thio]-1H-benzimidazole using cumene hydroperoxide with the addition of a base, according to one aspect of the present invention.

The experiment was performed using the same conditions as in Reference Example C with the additional feature that one equivalent of diisopropylethylamine was added together with the cumene hydroperoxide. After 3 h and 20 minutes the mixture consisted of 17.2% sulphide, 3.5% sulphone, 8.7% (−)-enantiomer of sulphoxide and 69.3% (+)-enantiomer of sulphoxide (i.e. ee=78%).

Reference Example E

Asymmetric synthesis of (+)-2-[5-(3,5-dimethylpyrazol-1-yl)pentylsulphinyl]-4,5-diphenylimidazole.

0.8 g (1.9 mmol) of 2-[5-(3,5-dimethylpyrazol-1-yl)pentylthio]-4,5-diphenylimidazole was dissolved in toluene (20 ml). The solution was concentrated on a rotavapor until half the volume was removed. To the mixture was added 20 μl (1.1 mmol) of water, 1.0 g (4.8 mmol) of (+)-diethyl L-tartrate and 0.54 g (1.9 mmol) of titanium(IV) isopropoxide in the given order. The mixture was stirred for 60 minutes at 50° C. and then 0.25 g (1.9 mmol) of N,N-diisopropylethylamine was added. The mixture was then stirred at room temperature for 30 minutes whereupon 0.36 g (80%, 1.9 nmuol) of cumene hydroperoxide was added. The mixture was stirred for four hours at room temperature and then the reaction was shown to be completed. The solution was washed with water (2 ml) and then the organic layer was removed. The oily residue was purified by chromatography on silica gel (methanol-methylene chloride 0 to 5%). There was obtained 0.7 g of the desired product as an oil which was shown to have an optical purity of 87% e.e.

Reference Example F

Asymmetric synthesis of (−)-2-[5-(3,5-dimethylpyrazol-1-yl)pentylsulphinyl]-4,5-diphenylimidazole.

1.5 g (3.6 mmol) of 2-[5-(3,5-dimethylpyrazol-1-yl)pentylthio]-4,5-diphenylimidazole was dissolved in toluene (40 ml). The solution was concentrated on a rotavapor until half the volume was removed. To the mixture was added 38 μl (2.1 mmol) of water, 1.85 g (9.0 mmol) of (−)-diethyl D-tartrate and 1.01 g (3.6 mmol) of titanium(IV) isopropoxide in the given order. The mixture was stirred for 60 minutes at 50° C. The mixture was divided in two parts and then 0.23 g (1.9 mmol) of N,N-diisopropylethylamine was added to half the mixture. This mixture was then stirred at room temperature for 15 minutes whereupon 0.35 g (80%, 1.8 mmol) of cumene hydroperoxide was added. The mixture was stirred for four hours at room temperature and then the reaction was shown to be completed. The solution was stirred with water (2 ml) and then the organic layer was removed. The oily residue was purified by chromatography on silica gel (methanol-methylene chloride 0 to 5%). There was obtained 0.65 g of the desired product as an oil which was shown to have an optical purity of 92% e.e.

Conclusion

The examples show that the highest enantiomeric excess is obtained if all aspects of the invention are taken into consideration. The addition of a base during the oxidation is essential for a high enantioselectivity according to one aspect of the invention. But a high enantiomeric excess may also be obtained according to other aspects of the invention if the order of addition of components into the reaction vessel is altered, and alternatively the time and/or temperature during the preparation of the chiral titanium complex is taken into consideration. The preparation of the chiral titanium complex is preferably performed in the presence of the prochiral sulphide and during an elevated temperature and a prolonged time.

Determination of enantiomeric excess in the Examples and Reference Examples

The enantiomeric excess value in each example given above gives an indication of the relative amounts of each enantiomer obtained. The value is defined as the difference between the relative percentages for the two enantiomers. Thus, for example, when the percentage of the (−)-enantiomer of the formed sulphoxide is 97.5% and the percentage for the (+)-enantiomer is 2.5%, the enantiomeric excess for the (−)-enantiomer is 95%.

The enantiomeric composition of the obtained sulphoxide has been determined by chiral High Performance Liquid Chromatography(HPLC) on either a Chiralpak AD Column® or a Chiral AGP Column® under the following conditions, specified for each compound:

Compound of formula (Ia)

| Column | Chiralpak AD 50 × 4.6 mm |
|---|---|
| Eluent | iso-Hexane (100 ml), ethanol (100 ml) and acetic acid (10 μl) |
| Flow | 0.5 ml/min |
| Inj.vol. | 50 μl |
| Wavelength | 302 nm |

Retention time for the (−)-enantiomer 4.0 min
Retention time for the (+)-enantiomer 5.8 min Compound of formula (Ib)

| Column | Chiralpak AD 50 × 4.6 mm |
|---|---|
| Eluent | iso-Hexane (125 ml), 2-propanol (25 ml), ethanol (50 ml) and acetic acid (30 μl) |
| Flow | 0.4 ml/min |
| Inj.vol. | 50 μl |
| Wavelength | 287 nm |

Retention time for the (+)-enantiomer 6.5 min
Retention time for the (+)-enantiomer 13.8 min Compound of formula (Ic)

| Column | Chiralpak AD 50 × 4.6 mm |
|---|---|
| Eluent | iso-Hexane (100 ml), ethanol (100 ml) and acetic acid (10 μl) |
| Flow | 0.4 ml/min |
| Inj.vol. | 50 μl |
| Wavelength | 300 nm |

Retention time for the (+)-enantiomer 6.4 min
Retention time for the (−)-enantiomer 9.4 min Compound of formula (Id)

| Column | Chiral-AGP 100 × 4.0 mm |
|---|---|
| Eluent | Sodium phosfate buffer solution (pH 7.0) I = 0.025 (500 ml) and acetonitrile (70 ml) |
| Flow | 0.5 ml/min |
| Inj.vol. | 20 μl |
| Wavelength | 210 nm |

Retention time for the (+)-enantiomer 6.2 min
Retention time for the (−)-enantiomer 7.2 min Compound of formula (Ie)

| Column | Chiralpak AD 50 × 4.6 mm |
|---|---|
| Eluent | iso-Hexane (150 ml), ethanol (50 ml) and acetic acid (10 μl) |
| Flow | 0.5 ml/min |
| Inj.vol. | 50 μl |
| Wavelength | 290 nm |

Retention time for the (−)-enantiomer 9.5 min
Retention time for the (+)-enantiomer 13.3 min Compound of formula (If)

| Column | Chiral-AGP 100 × 4.0 mm |
|---|---|
| Eluent | Sodium phosfate buffer solution (pH 7.0) I = 0.025 (430 ml) and acetonitrile (70 ml) |
| Flow | 0.5 ml/min |
| Inj.vol. | 20 μl |
| Wavelength | 210 nm |

Retention time for the (+)-enantiomer 4.1 min
Retention time for the (−)-enantiomer 6.8 min
Compound of formula (Ig)

| Column | Chiralpak AD 50 × 4.6 mm |
|---|---|
| Eluent | iso-Hexane (200 ml) and ethanol (10 ml) |
| Flow | 0.5 ml/min |
| Inj.vol. | 50 μl |
| Wavelength | 285 nm |

Retention time for the (−)-enantiomer 9.0 min
Retention time for the (+)-enantiomer 9.8 min
Compound of formula (Ih)

| Column | Chiralpak AD 50 × 4.6 mm |
|---|---|
| Eluent | iso-Hexane (150 ml) and 2-propanol (50 ml) |
| Flow | 0.4 ml/min |
| Inj.vol. | 50 μl |
| Wavelength | 285 nm |

Retention time for the (−)-enantiomer of diasteremor A 6.9 min
Retention time for the (+)-enantiomer of diasteremor A 8.1 min
Retention time for the (+)-enantiomer of diasteremor B 8.8 min
Retention time for the (−)-enantiomer of diasteremor B 11.0 min The first diastereomer of compound (Ih) eluted on straight phase (achiral silica gel, see below) is named diastereomer A and second as diastereomer B.

Reference Examples E and F

In Reference Examples E and F, the enantiomeric composition of the products was determined by chiral HPLC using following conditions:

| Column | Chiralpak AD 50 × 4.6 mm |
|---|---|
| Eluent | iso-Hexane (200 ml), ethanol (5 ml) and acetic acid (10 μl) |
| Flow | 1 ml/min |
| Inj.vol | 50 μl |
| Wave lenght | 280 nm |

Retention time for the (+)-enantiomer 13.5 min
Retention time for the (−)-enantiomer 17.3 min It is to be noted that in the Examples referring to the single enantiomers of omeprazole or its alkaline salts, the sign of the optical rotation of single enantiomeric form of omeprazole sodium salt measured in water is the opposite of that of the sign when measured said compound in its neutral form in chloroform.

We claim:

1. A process for enantioselective synthesis of a sulfoxide compound of formula (I) or an alkaline salt thereof in the form of a single enantiomer or in an enantiomerically enriched form

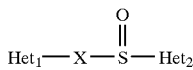

I wherein

Het₁ is

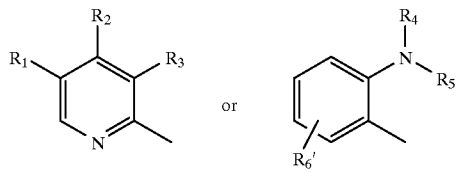

Het₂ is

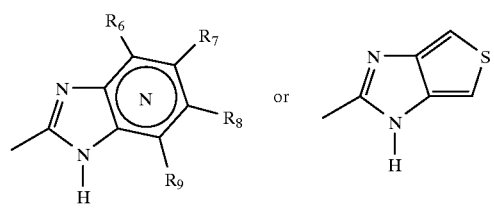

and X is

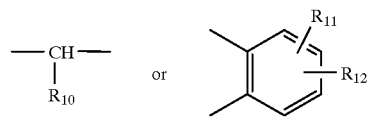

wherein

N inside the benzene ring of the benzimidazole moiety means that one of the ring carbon atoms substituted by $R_6$–$R_9$ may be exchanged by a nitrogen atom without the substituents;

$R_1$, $R_2$ and $R_3$ are the same or different and selected from the group consisting of hydrogen, alkyl, alkylthio and alkoxy, wherein the alkyl, alkylthio and alkoxy are unsubstituted or substituted by fluorine, alkoxyalkoxy, dialkylamino, piperidino, morpholino, halogen, phenylalkyl and phenylalkoxy;

$R_4$ and $R_5$ are the same or different and selected from the group consisting of hydrogen, alkyl and aralkyl;

$R_6'$ is hydrogen, halogen, trifluoromethyl, alkyl and alkoxy;

$R_6$–$R_9$ are the same or different and selected from the group consisting of hydrogen, alkyl alkoxy, halogen, halo-alkoxy, alkyl-carbonyl, alkoxy carbonyl, oxazolyl, and trifluoroalkyl, or adjacent $R_6$–$R_9$ groups form ring structures which are unsubstituted or substituted;

$R_{10}$ is hydrogen or forms an alkylene chain together with $R_3$;

$R_{11}$ and $R_{12}$ are the same or different and selected from the group consisting of hydrogen, halogen, alkyl and alkoxy, wherein the alkyl and alkoxy are independently branched or a straight $C_1$–$C_9$ chain or a cyclic alkyl, which process comprises oxidizing a pro-chiral sulfide of the formula II

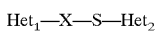

wherein Het$_1$ and Het$_2$ are as defined above, in an organic solvent with an oxidizing agent and in presence of a chiral titanium complex and a base, and optionally converting the obtained sulfoxide into a pharmaceutically acceptable salt by a conventional process.

2. A process for enantioselective synthesis of a sulfoxide compound of formula I or an alkaline salt thereof in the form of a single enantiomer or in an enantiomerically enriched form

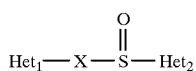

wherein
Het$_1$ is

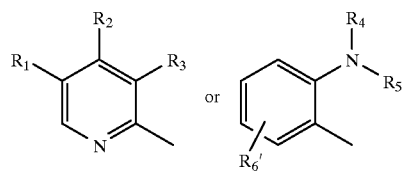

Het$_2$ is

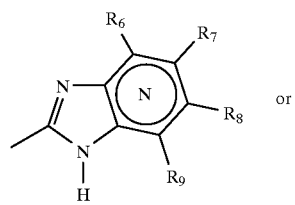

and X is

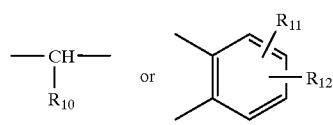

wherein
N inside the benzene ring of the benzimidazole moiety means that one of the ring carbon atoms substituted by R$_6$–R$_9$ may be exchanged by a nitrogen atom without the substituents;
R$_1$, R$_2$ and R$_3$ are the same or different and selected from the group consisting of hydrogen alkyl, alkylthio and alkoxy, wherein the alkyl, alkylthio and alkoxy are unsubstituted or substituted by fluorine, alkoxyalkoxy, dialkylamino, piperidino, morpholino, halogen, phenylalkyl and phenylalkoxy;
R$_4$ and R$_5$ are the same or different and selected from the group consisting of hydrogen, alkyl and aralkyl;
R$_6$' is hydrogen, halogen, trifluoromethyl, alkyl and alkoxy;
R$_6$–R$_9$ are the same or different and selected from the group consisting of hydrogen, alkyl, alkoxy, halogen, halo-alkoxy, alkyl-carbonyl, alkoxy carbonyl, oxazolyl and trifluoroalkyl, or adjacent R$_6$–R$_9$ groups form ring structures which are unsubstituted or substituted;
R$_{10}$ is hydrogen or forms an alkylene chain together with R$_3$;
R$_{11}$ and R$_{12}$ are the same or different and selected from the group consisting of hydrogen, halogen, alkyl and alkoxy, wherein the alkyl and alkoxy are independently branched or a straight C$_1$–C$_9$ chain or a cyclic alkyl,
which process comprises oxidizing a pro-chiral sulfide of the formula II

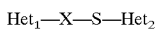

wherein Het$_1$ and Het$_2$ are as defined above, in an organic solvent with an oxidizing agent and in the presence of a chiral titanium complex, wherein the titanium complex has been prepared in the presence of the pro-chiral sulfide, and optionally converting the obtained sulfoxide into a pharmaceutically acceptable salt by a conventional process.

3. A process for enantioselective synthesis of a sulfoxide compound of formula I or an alkaline salt thereof in the form of a single enantiomer or in an enantiomerically enriched form

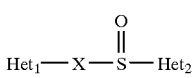

wherein
Het$_1$ is

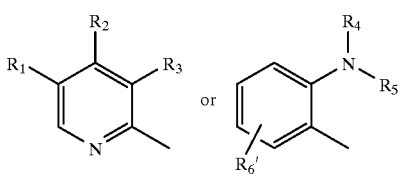

Het$_2$ is

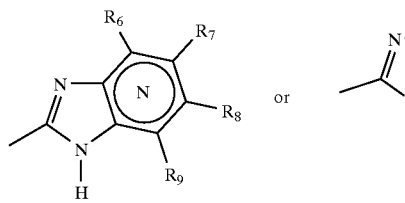

and X is

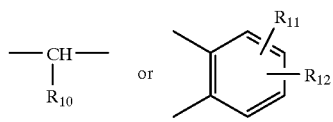

wherein
N inside the benzene ring of the benzimidazole moiety means that one of the ring carbon atoms substituted by R$_6$–R$_9$ may be exchanged by a nitrogen atom without the substituents:
R$_1$, R$_2$ and R$_3$ are the same or different and selected from the group consisting of hydrogen, alkyl, alkylthio and alkoxy, wherein the alkyl, alkythio and alkoxy are unsubstituted or substituted by fluorine, alkoxyalkoxy, dialkylamino, piperidino, morpholino, halogen, phenylalkyl and phenylakoxy;

$R_4$ and $R_5$ are the same or different and selected from the group consisting of hydrogen, alkyl and aralkyl;

$R_6'$ is hydrogen, halogen, trifluoromethyl, alkyl and alkoxy;

$R_6$–$R_9$ are the same or different and selected from the group consisting of hydrogen, alkyl, alkoxy, halogen, halo-alkoxy, alkylcarbonyl, alkoxycarbonyl, oxazolyl and trifluoroalkyl, or adjacent $R_6$–$R_9$ groups form ring structures which are unsubstituted or substituted;

$R_{10}$ is hydrogen or form an alkylene chain together with $R_3$;

$R_{11}$ and $R_{12}$ are the same or different and selected from the group consisting of hydrogen, halogen, alkyl and alkoxy, wherein the alkyl and alkoxy are independently branched or a straight $C_1$–$C_9$ chain or a cyclic alkyl, which process comprises oxidizing a pro-chiral sulfide of the formula II $$Het_1\text{—}X\text{—}S\text{—}Het_2 \qquad II$$

wherein $Het_1$ and $Het_2$ are as defined above, in an organic solvent with an oxidizing agent and in the presence of a chiral titanium complex, wherein the titanium complex has been prepared during an elevated temperature or a prolonged preparation time or both, and optionally converting the obtained sulfoxide into a pharmaceutically acceptable salt by a conventional process.

4. A process for enantioselective synthesis of a sulfoxide compound of formula I or an alkaline salt thereof in the form of a single enantiomer or in an enantiomerically enriched form $$Het_1\text{—}X\text{—}\overset{\overset{O}{\|}}{S}\text{—}Het_2 \qquad I$$

wherein $Het_1$ is or $Het_2$ is or and X is $$\text{—}\underset{\underset{R_{10}}{|}}{CH}\text{—} \quad \text{or} \quad$$

wherein

N inside the benzene ring of the benzimidazole moiety means that one of the ring carbon atoms substituted by $R_6$–$R_9$ may be exchanged by a nitrogen atom without the substituents;

$R_1$, $R_2$ and $R_3$ are the same or different and selected from the group consisting of hydrogen, alkyl, alkylthio and alkoxy, wherein the alkyl, alkylthio and alkoxy are unsubstituted or substituted by fluorine, alkoxyalkoxy, dialkylamino, piperidino, morpholino, halogen, phenylalkyl and phenylalkoxy;

$R_4$ and $R_5$ are the same or different and selected from the group consisting of hydrogen, alkyl and aralkyl;

$R_6'$ is hydrogen, halogen, trifluoromethyl, alkyl and alkoxy;

$R_6$–$R_9$ are the same or different and selected from the group consisting of hydrogen, alkyl, alkoxy, halogen, halo-alkoxy, alkylcarbonyl, alkoxycarbonyl, oxazolyl and trifluoroalkyl, or adjacent $R_6$–$R_9$ groups form ring structures which are unsubstituted or substituted;

$R_{10}$ is hydrogen or form an alkylene chain together with $R_3$;

$R_{11}$ and $R_{12}$ are the same or different and selected from the group consisting of hydrogen, halogen, alkyl and alkoxy, wherein the alkyl and alkoxy are independently branched or a straight $C_1$–$C_9$ chain or a cyclic alkyl, which process comprises oxidizing a pro-chiral sulfide of the formula II $$Het_1\text{—}X\text{—}S\text{—}Het_2 \qquad II$$

wherein $Het_1$ and $Het_2$ are as defined above, in an organic solvent with an oxidizing agent and in the presence of a chiral titanium complex, wherein the titanium complex is prepared in the presence of the pro-chiral sulfide and during an elevated temperature or during a prolonged preparation time, or both, and optionally converting the obtained sulfoxide into a pharmaceutically acceptable salt by a conventional process.

5. A process according to any of claims 1–4, wherein the sulphoxides prepared by the process are sulphoxides defined by formula I' in the form of a single enantiomer or in an enantiomerically enriched form:

(I')

wherein

Ar is

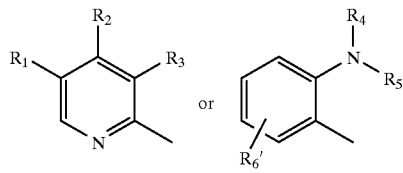

or and R$_1$–R$_{10}$ are the same as defined.

6. A process according to any of claims 1–4, wherein the sulfoxide is according to any of the formula (Ia) to (Ih) in the form of a single enantiomer or in an enantiomerically enriched form:

(Ia)
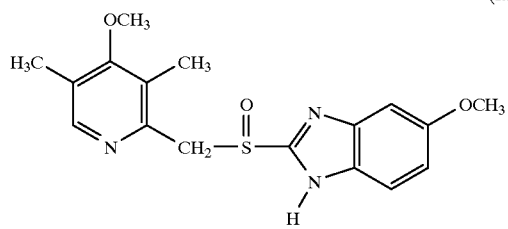

(Ib)
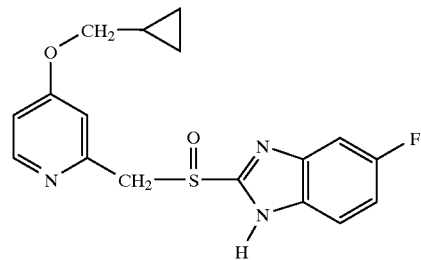

(Ic)
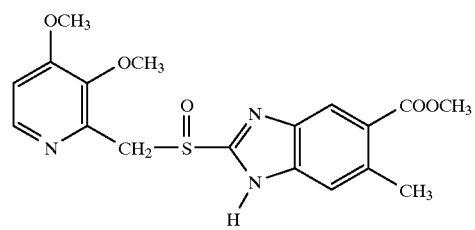

(Id)
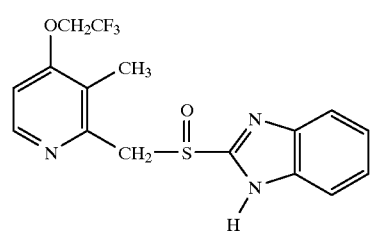

(Ie)
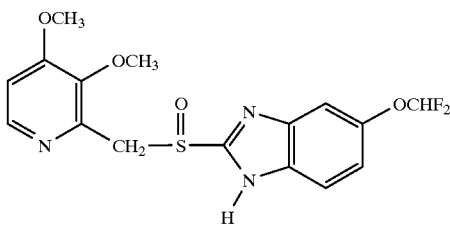

(If)
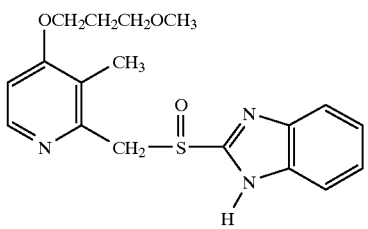

(Ig)
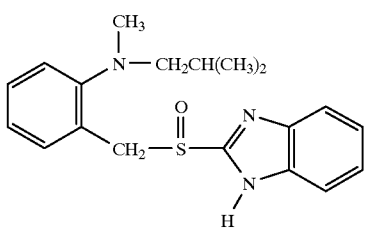

(Ih)
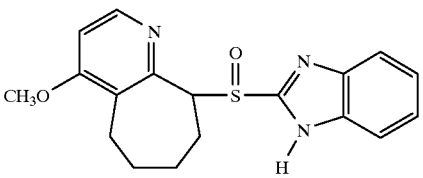

7. A process according to any of claims 1–4, wherein the pro-chiral sulphide of formula II is oxidised with an oxidising agent in the form of cumene hydroperoxide.

8. A process according to any of claims 1–4, wherein the titanium complex is prepared from a titanium(IV) compound.

9. A process according to any of the claims 1–4 wherein the titanium(IV) compound is a titanium(IV) alkoxide.

10. A process according to anyone of the claims 1–4 wherein the titanium(IV) alkoxide is titanium(IV) isopropoxide.

11. A process according to any of claims 1–4, wherein the chiral ligand in the titanium complex is a chiral branched or unbranched alkyl diol or an aromatic diol.

12. A process according to anyone of the claims 1–4 wherein the chiral diol is a chiral ester of tartaric acid.

13. A process according to anyone of the claims 1–4 wherein the chiral ester is selected from the group of (+)-diethyl L-tartrate and (−)-diethyl D-tartrate.

14. A process according to any of claims 1–4 wherein the amount of chiral titanium complex is 0.05–0.50 equivalents.

15. A process according to any of claims 1–4, characterized in that the oxidation reaction is carried out at a temperature between 20–40° C.

16. A process according to any of claims 1–4, wherein the organic solvent is selected from the group of toluene and ethyl acetate.

17. The process according to any of the claims 2–4, wherein the oxidization of the pro-chiral sulfide takes place in the presence of a base.

18. A process according to claim 1 or 7, wherein the base is an organic base.

19. A process according to claim 18, wherein the base is an amine.

20. A process according to claim 19, wherein the amine is selected from the group of triethylamine and N,N-diisopropylethylamine.

21. A process according to any of claims 1–4 wherein the prolonged preparation time for preparation of the chiral titanium complex is 1–5 hours.

22. A process according to any of claims 1–4, wherein the an elevated temperature for preparation of the chiral complex is 30–70° C.

23. A process according to any one of claims 1–4, wherein the process further comprises the step of treating the product of the oxidation reaction with an aqueous ammonia solution.

24. A process according to any of claims 1–4, wherein the process further comprises steps for crystallisation of the obtained crude product.

25. The process according to anyone of the claims 1–4, wherein the sulfoxide compound is (+)-5methoxy-2-(((4-methoxy-3,5-dimethyl-2-pyridinyl)-methyl)sulfinyl-1H-benzimidazole or a pharmaceutrically acceptable sat thereof.

26. The process according to any of the claims 1–4, wherein the sulfoxide compound is (−)-5-methoxy-2-(((4-methoxy-3,5-dimethyl-2-pyridinyl)-methyl)sulfinyl)-1H-benzimidazole or a pharmaceutrically acceptable sat thereof.

27. The process according to any one of claims 1–4, wherein the sulfoxide compound is (+)-5fluoro-2-[[(4-cyclopropylmethoxy-2-pyridinyl)-methyl]sulphinyl]-1H-benzimidazole or a pharmaceutically acceptable salt thereof.

28. The process according to any one of claims 1–4, wherein the sulfoxide compound is (−)-5fluoro-2-[[(4-cyclopropylmethoxy-2-pyridinyl)-methyl]sulphinyl]-1H-benzimidazole or a pharmaceutically acceptable salt thereof.

29. The process according to any one of claims 1–4, wherein the sulfoxide compound is (+)-5carbomethoxy-6-methyl-2-[[(3,4-dimethoxy-2-pyridinyl)-methyl]sulphinyl]-1H-benzimidazole or a pharmaceutically acceptable salt thereof.

30. The process according to any one of claims 1–4, wherein the sulfoxide compound is (−)-5carbomethoxy-6-methyl-2-[[(3,4-dimethoxy-2-pyridinyl)-methyl]sulphinyl]-1H-benzimidazole or a pharmaceutically acceptable salt thereof.

31. One of the single enantiomers of 2(((4-(3-methoxypropoxy)-3-methyl-2-pyridinyl)methyl)sulphinyl)-1H-benzimidazole or a pharmaceutically acceptable salt thereof.

32. One of the single enantiomers of 2(2-(N-isobutyl-N-methylamino)benzimidazole or a pharmaceutically acceptable salt thereof.

33. One of the single enantiomers of the more lipophilic diastereomer of 2((4-methoxy-6,7,8,9-tetrahydro-5H-cyclohepta(b)pyridin-9-yl)-sulfinyl-1H-benzimidazole or a pharmaceutically acceptable salt thereof.

34. One of the single enantiomers of the less lipophilic diastereomer of 2((4-methoxy-6,7,8,9-tetrahydro-5H-cyclohepta(b)pyridin-9-yl)-sulfinyl)-1H-benzimidazole or a pharmaceutically acceptable salt thereof.

35. A method for the treatment of gastrointestinal diseases comprising the administration to a mammal including man in need of such treatment of a pharmaceutical preparation comprising an effective amount of the sulfoxide compound of any one of claims 31–34 and a pharmaceutically acceptable carrier.

* * * * *

UNITED STATES PATENT AND TRADEMARK OFFICE
CERTIFICATE OF CORRECTION

PATENT NO.  : 5,948,789
DATED       : September 7, 1999
INVENTOR(S) : Larsson et al.

It is certified that error appears in the above-identified patent and that said Letters Patent is hereby corrected as shown below:

In claim 1, col. 27, line 5: after the word "in", insert -- the --.

In claim 10, col. 32, line 50: delete "anyone" and insert therefor -- any --.

In claim 12, col. 32, line 56: delete "anyone" and insert therefor -- any --.

In claim 13, col. 32, line 58: delete "anyone" and insert therefor -- any --.

In claim 18, col. 33, line 4: delete "7", and insert therefor -- 17 --.

In claim 21, col. 33, line 11: delete "any of claims 1-4", and insert therefor -- claim 3 or 4--.

In claim 22, col. 33, line 14: delete "any of claims 1-4", and insert therefor -- claim 3 or 4--.

In claim 25, col. 33, line 23: delete "anyone" and insert therefor -- any --; and in line 25, after "sulfinyl", insert --) --.

In claim 32, col. 34, line 20: after "methylaminio", insert -- benzylsulfinyl)--.

Signed and Sealed this

Fourteenth Day of March, 2000

Attest:

Q. TODD DICKINSON

*Attesting Officer*     Commissioner of Patents and Trademarks

UNITED STATES PATENT AND TRADEMARK OFFICE
CERTIFICATE OF CORRECTION

PATENT NO. : 5,948,789
DATED : September 7, 1999
INVENTOR(S) : Larsson et al.

It is certified that error appears in the above-identified patent and that said Letters Patent is hereby corrected as shown below:

Column 26,
Delete lines 64-67, and substitute therefore:
$R_{11}$ and $R_{12}$ are the same or different and selected from the group consisting of hydrogen, halogen and alkyl, wherein the alkyl groups and alkoxy groups of the preceding substituents $R_1$ to $R_{12}$ are optionally independently branched or a straight $C_1$-$C_9$ chain or a cyclic alkyl, Column 28,
Delete lines 6-9 and substitute therefor:
$R_{11}$ and $R_{12}$ are the same or different and selected from the group consisting of hydrogen, halogen and alkyl, wherein the alkyl groups and alkoxy groups of the preceding substituents $R_1$ to $R_{12}$ are optionally independently branched or a straight $C_1$-$C_9$ chain or a cyclic alkyl, Column 29,
Delete lines 18-21, and substitute therefor:
$R_{11}$ and $R_{12}$ are the same or different and selected from the group consisting of hydrogen, halogen and alkyl, wherein the alkyl groups and alkoxy groups of the preceding substituents $R_1$ to $R_{12}$ are optionally independently branched or a straight $C_1$-$C_9$ chain or a cyclic alkyl,

UNITED STATES PATENT AND TRADEMARK OFFICE
CERTIFICATE OF CORRECTION

PATENT NO. : 5,948,789
DATED : September 7, 1999
INVENTOR(S) : Larsson et al.

It is certified that error appears in the above-identified patent and that said Letters Patent is hereby corrected as shown below:

Column 30,
Delete lines 35-58, and substitute therefor:
$R_{11}$ and $R_{12}$ are the same or different and selected from the group consisting of hydrogen, halogen and alkyl, wherein the alkyl groups and alkoxy groups of the preceding substituents $R_1$ to $R_{12}$ are optionally independently branched or a straight $C_1$-$C_9$ chain or a cyclic alkyl, Signed and Sealed this Twenty-third Day of April, 2002

Attest:

JAMES E. ROGAN
*Director of the United States Patent and Trademark Office*

*Attesting Officer*